(12) United States Patent
Childers et al.

(10) Patent No.: US 8,236,240 B2
(45) Date of Patent: Aug. 7, 2012

(54) METHOD AND SYSTEM FOR CONDUCTING VAPOR PHASE DECONTAMINATION OF SEALABLE ENTITIES AND THEIR CONTENTS

(76) Inventors: James Arthur Childers, Trinity, FL (US); Robert Warren Childers, Trinity, FL (US)

( * ) Notice: Subject to any disclaimer, the term of this patent is extended or adjusted under 35 U.S.C. 154(b) by 1214 days.

(21) Appl. No.: 11/656,570

(22) Filed: Jan. 23, 2007

(65) Prior Publication Data

US 2007/0274858 A1    Nov. 29, 2007

Related U.S. Application Data

(60) Provisional application No. 60/777,072, filed on Feb. 25, 2006.

(51) Int. Cl.
| | |
|---|---|
| *A61L 9/00* | (2006.01) |
| *A61L 2/00* | (2006.01) |
| *A62B 7/08* | (2006.01) |
| *B05B 1/24* | (2006.01) |
| *B05B 1/08* | (2006.01) |
| *F22B 27/00* | (2006.01) |

(52) U.S. Cl. ......... 422/28; 422/1; 422/3; 422/5; 422/20; 422/31; 422/32; 422/124; 422/125; 422/292; 422/298; 422/305; 422/900; 392/386; 392/394; 392/399; 392/467; 122/40; 122/28; 122/412; 239/102.2; 239/136

(58) Field of Classification Search .................. 422/1, 3, 422/5, 20, 28, 31–32, 124–125, 292, 298, 422/305, 900; 392/386, 394, 399, 467; 122/40, 122/28, 412; 239/102.2, 136

See application file for complete search history.

(56) References Cited

U.S. PATENT DOCUMENTS

| | | | | |
|---|---|---|---|---|
| 3,245,461 A | * | 4/1966 | Allington | 165/228 |
| 3,767,362 A | * | 10/1973 | Griffin et al. | 422/27 |
| 4,909,436 A | * | 3/1990 | Hamner et al. | 236/44 A |
| 5,173,258 A | * | 12/1992 | Childers | 422/27 |
| 5,560,222 A | * | 10/1996 | Perron | 62/435 |
| 5,868,999 A | * | 2/1999 | Karlson | 422/30 |
| 5,872,359 A | * | 2/1999 | Stewart et al. | 250/339.12 |
| 2003/0086820 A1 | * | 5/2003 | McDonnell et al. | 422/28 |
| 2004/0191112 A1 | * | 9/2004 | Hill et al. | 422/3 |

* cited by examiner

*Primary Examiner* — Jill Warden
*Assistant Examiner* — Monzer Chorbaji

(57) ABSTRACT

The invention provides a method and system for conducting a continuous operation, flowing vapor phase decontamination in either an open loop or a closed loop. Using the method, a multi-component liquid decontaminant is vaporized and delivered into, through and out of a sealable enclosure by means of a carrier gas that is flowing into, through and out of said sealable enclosure. After leaving the enclosure, the vapor is captured in a cold-water bath and decomposed.

The invention humidifies the carrier gas by passing it through a temperature controlled water bath to warm, or to cool, the carrier gas as necessary in order to bring the carrier gas to the desired temperature and humidity before it is combined with the vaporized sterilant and allowed to flow into the sealable enclosure. The concentration of the vapor sterilant and the percent saturation of the vapor sterilant are simultaneously controlled by controlling the rate at which the carrier gas flows and the rate at which the liquid sterilant is vaporized. A chilled mirror or other type of dew point sensor can be used to ensure that near saturation conditions are maintained during decontamination.

20 Claims, 15 Drawing Sheets

Embodiment of Decontamination System

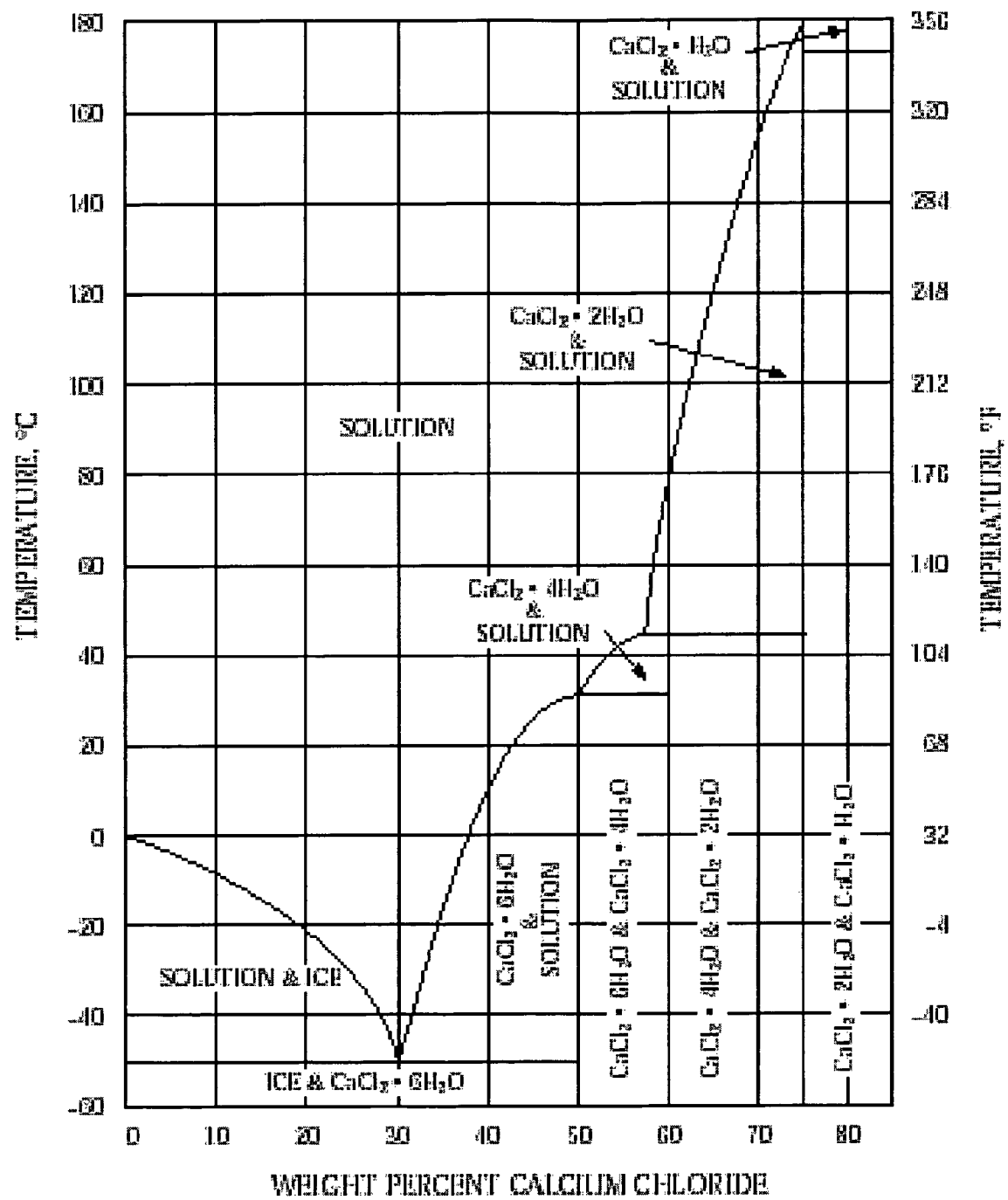
Figure 1: Phase Diagram for Calcium Chloride and Water Solutions

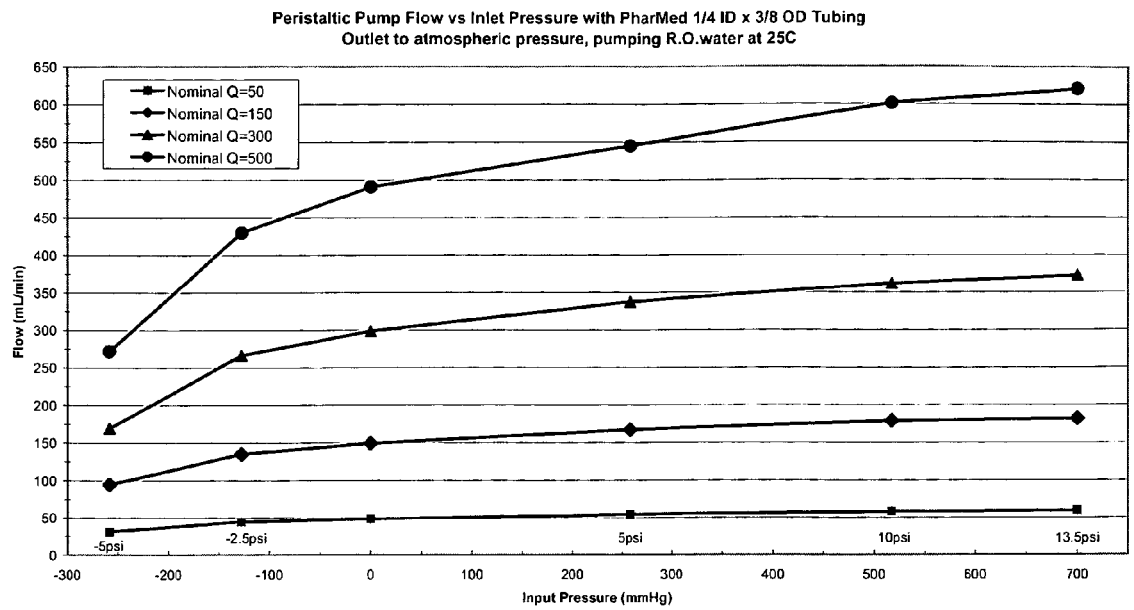
Figure 2: Peristaltic Pump Outlet Flow Variation over a Range of Inlet Pressures
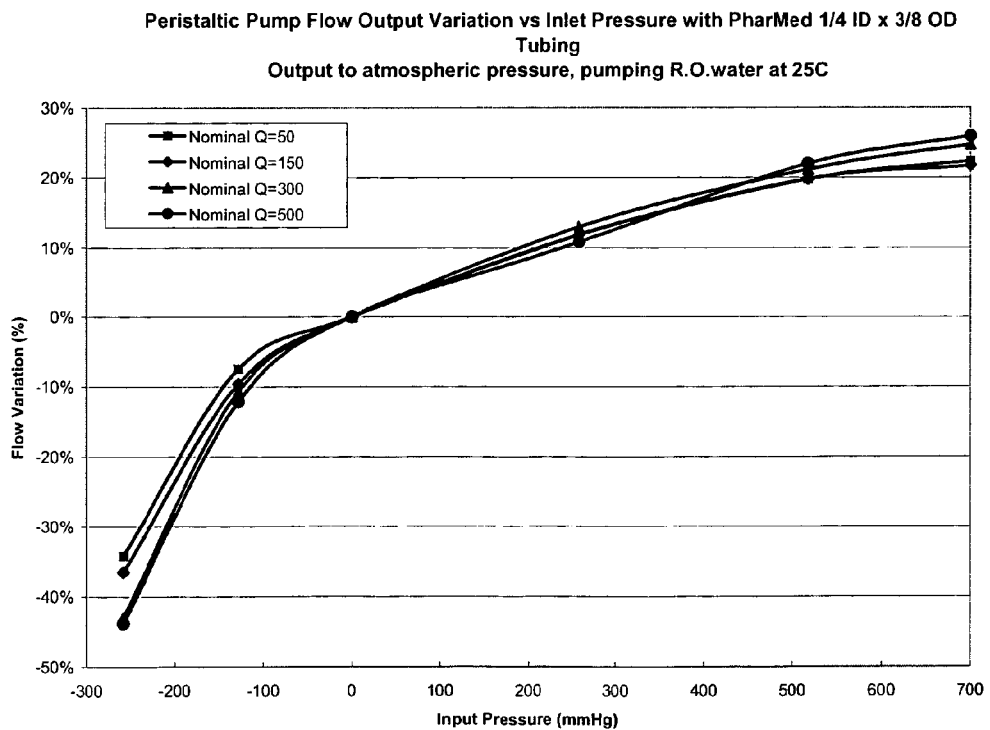
Figure 3: Ratio of Actual to Nominal Outlet Flow over a Range of Inlet Pressures

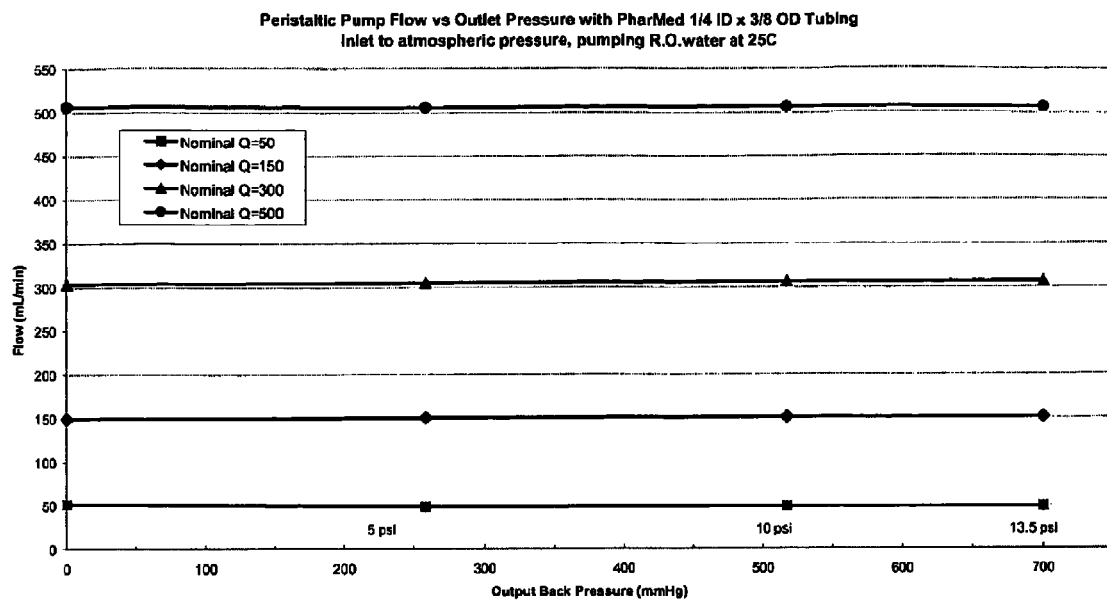
Figure 4: Peristaltic Pump Outlet Flow Variation over a Range of Outlet Pressures
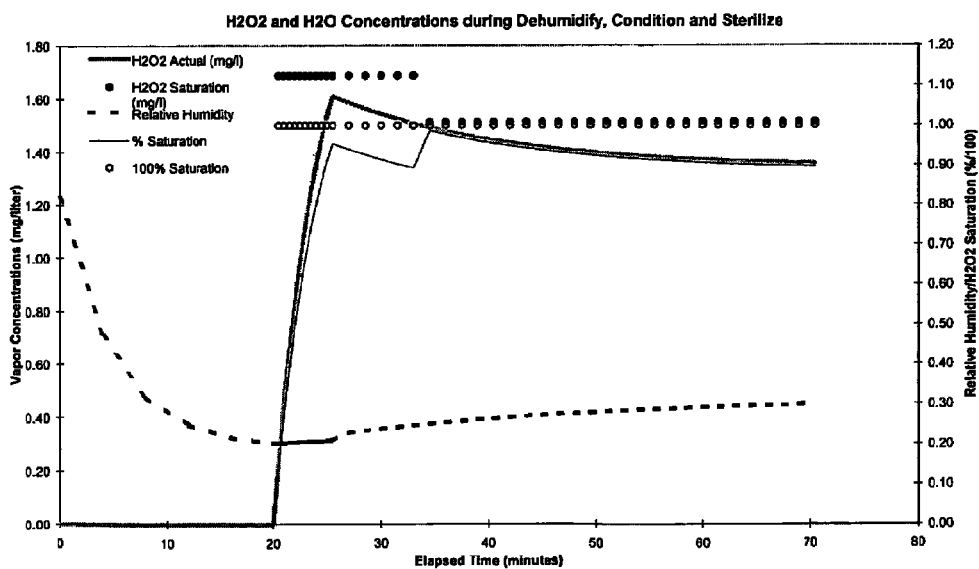
Figure 5: $H_2O_2$ vapor decontamination cycle without percent saturation feedback.

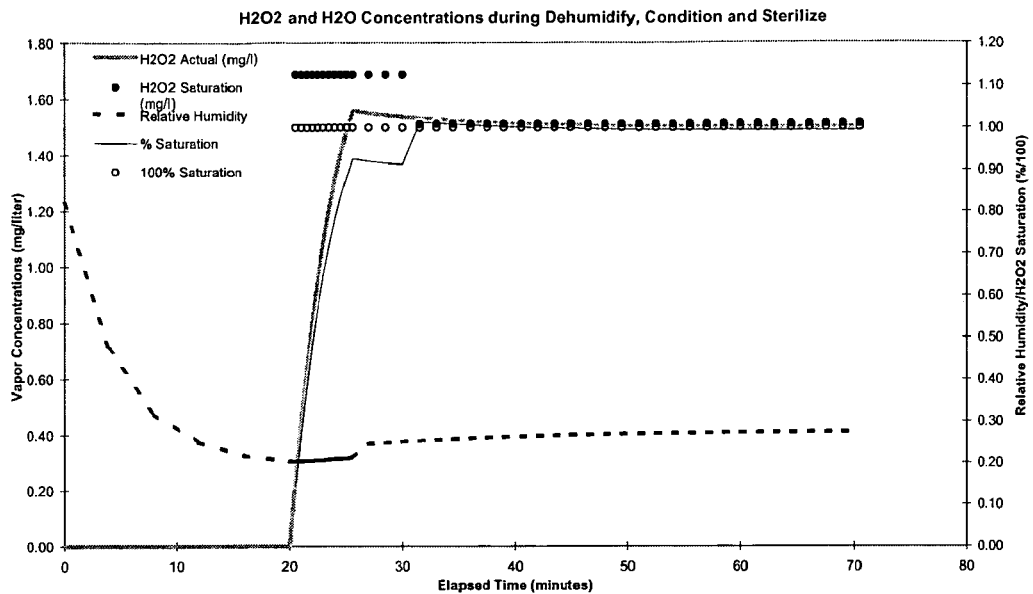
Figure 6: Decontamination cycle with 64 SCFM airflow rate has higher $H_2O_2$ vapor Concentration
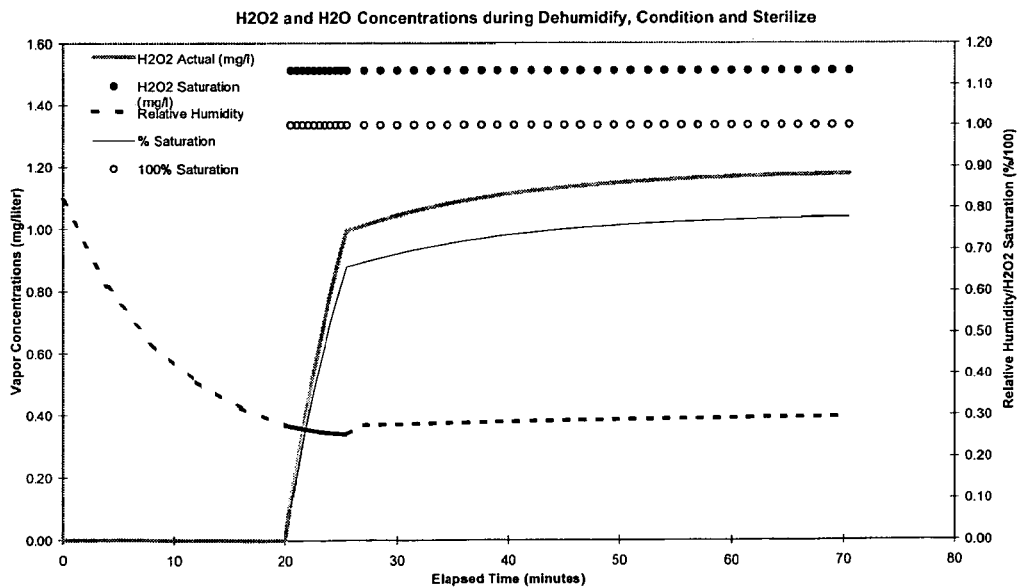
Figure 7: Decontamination cycle from Figure 6 applied to a 2000 cubic foot enclosure.

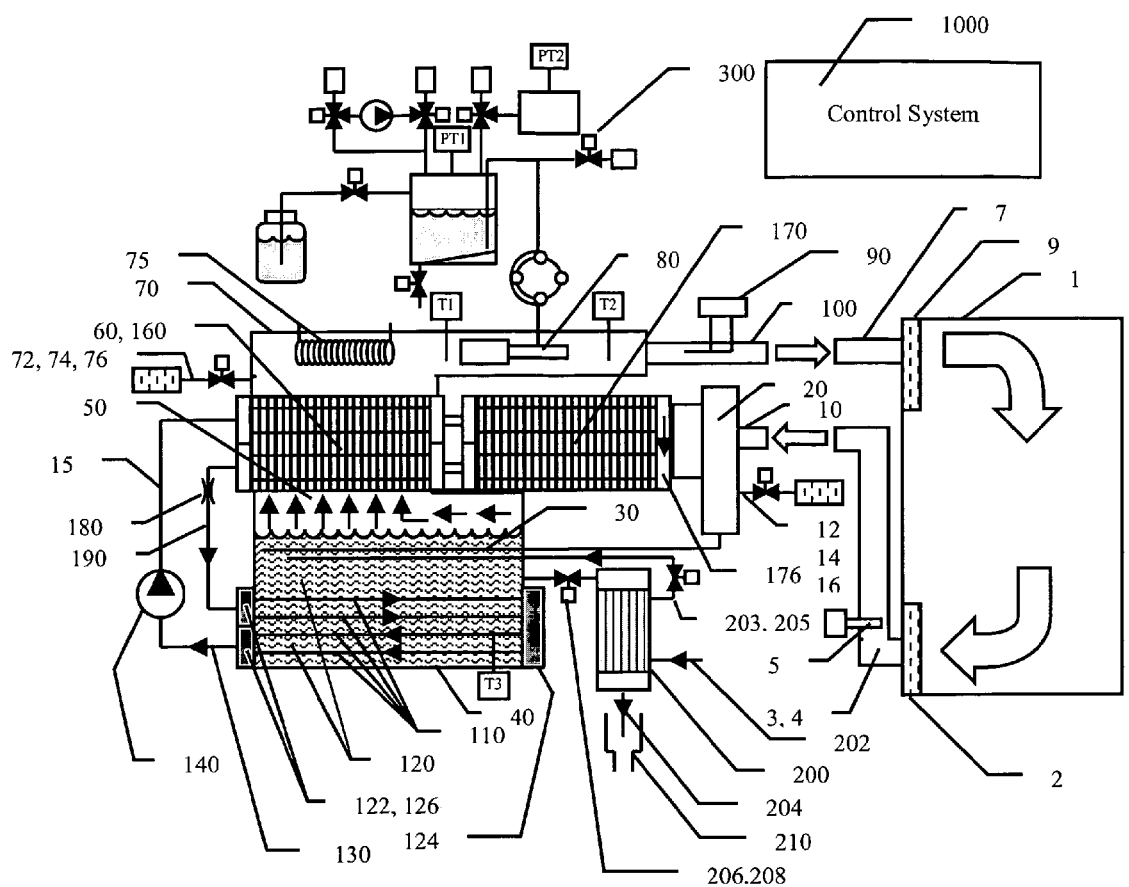
Figure 8: Embodiment of Decontamination System

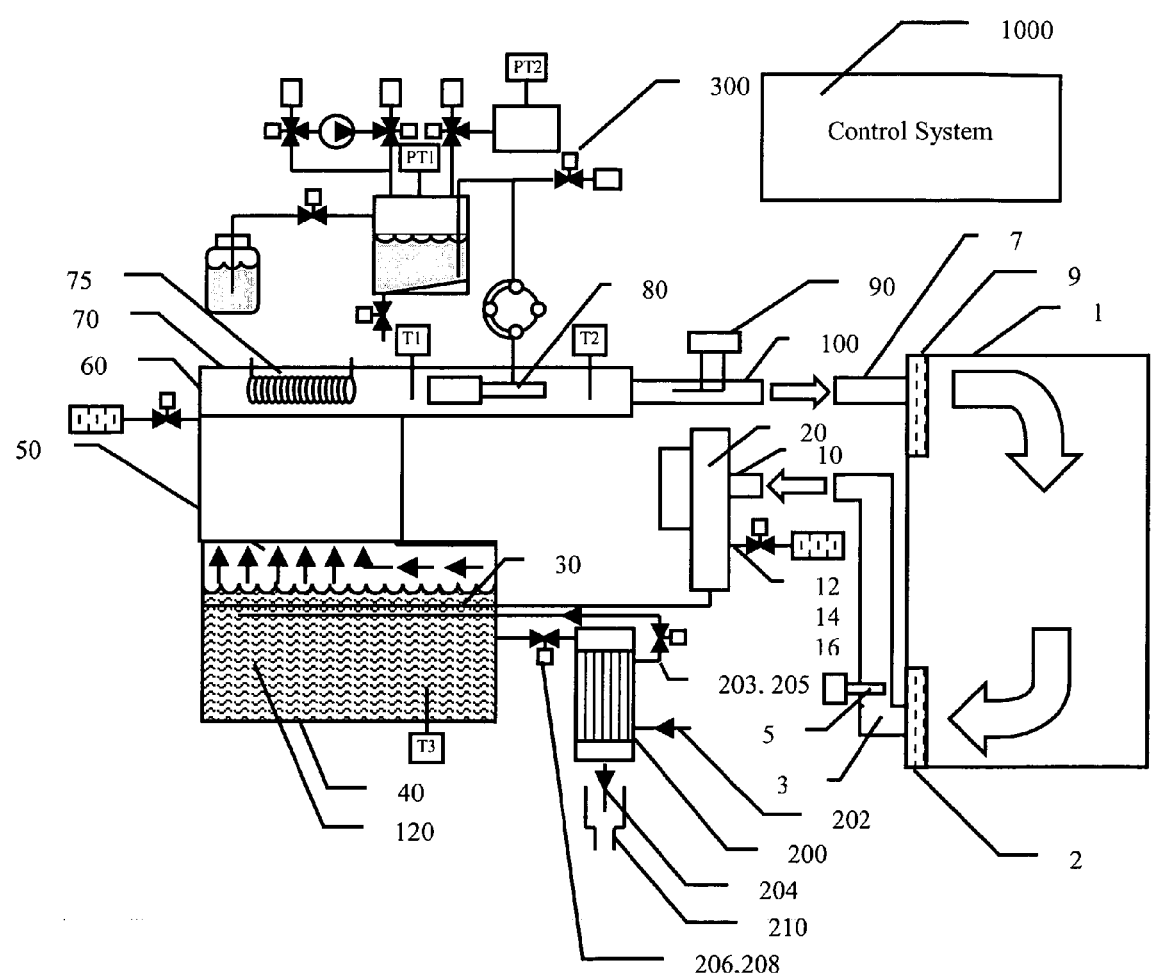
Figure 9: Alternate Lower Cost Embodiment of the Decontamination System

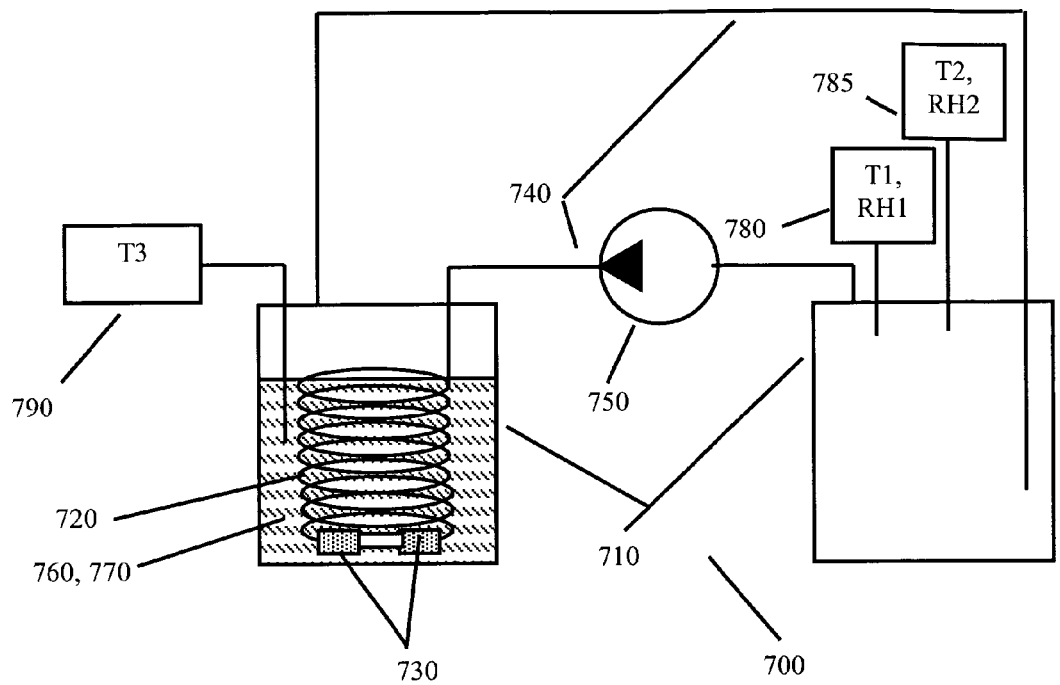
Figure 10: Closed Loop Humidification Test Set-up 700
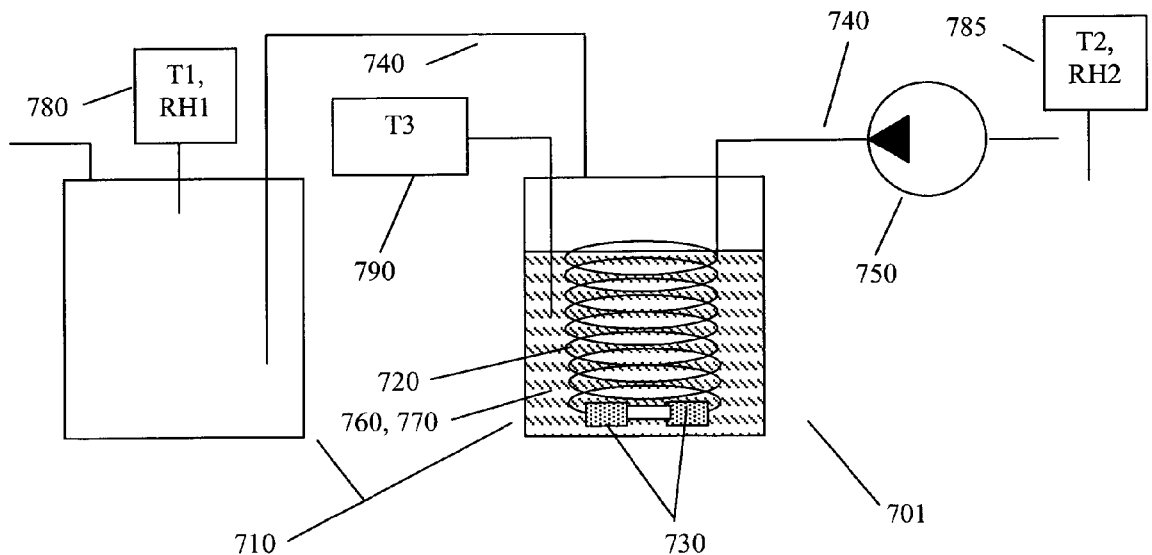
Figure 11: Open Loop Humidification Test Setup

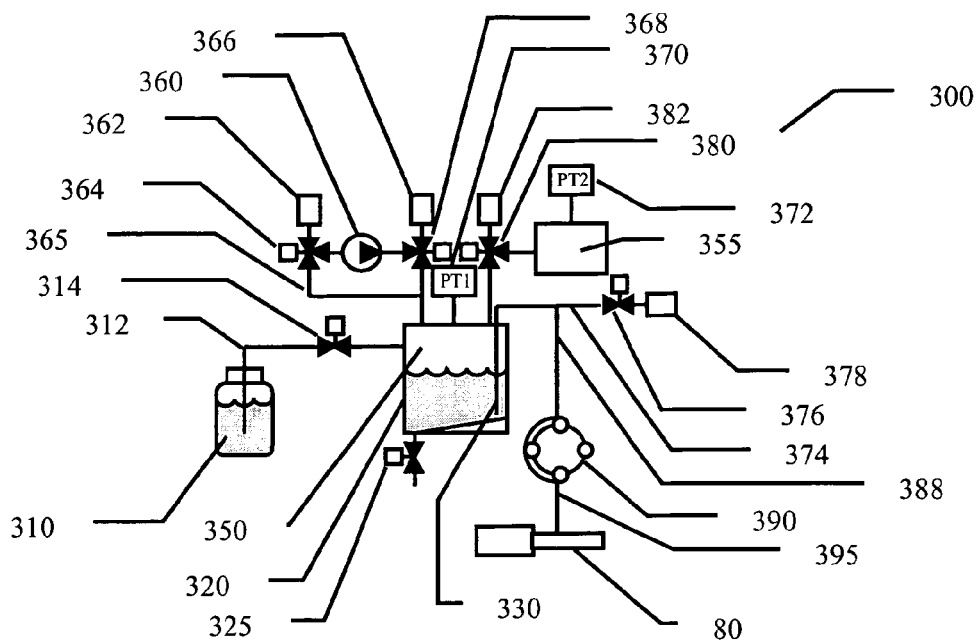
Figure 12: Embodiment of Liquid Sterilant Delivery System with Feedback Control
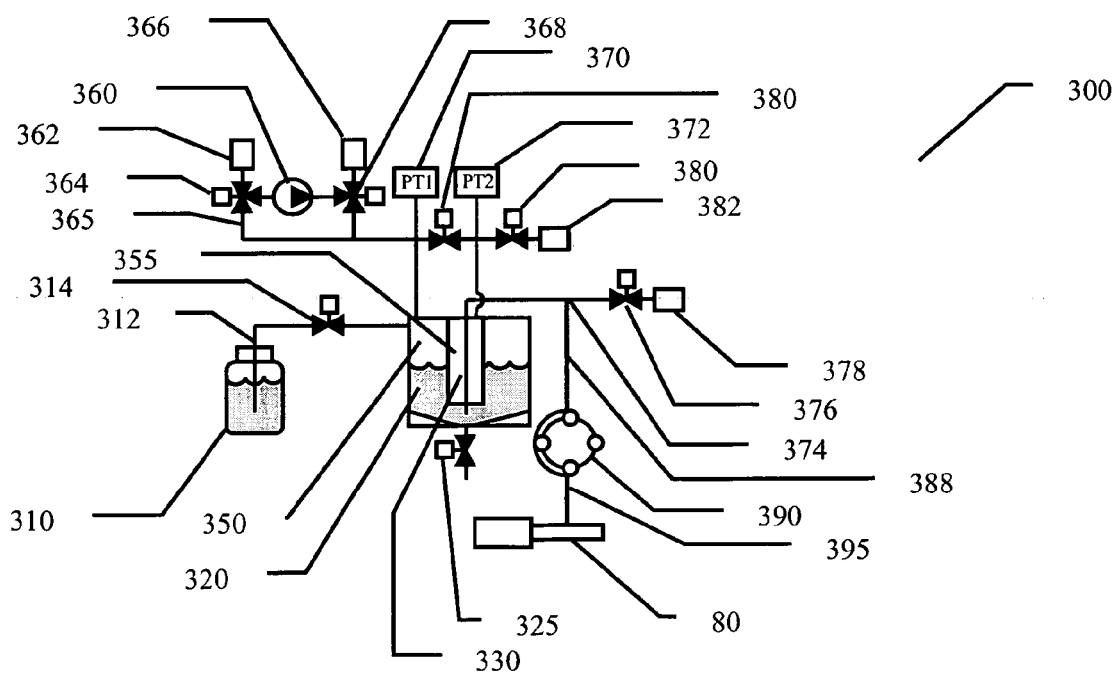
Figure 13: Alt Embodiment of Liquid Sterilant Delivery System with Feedback Control

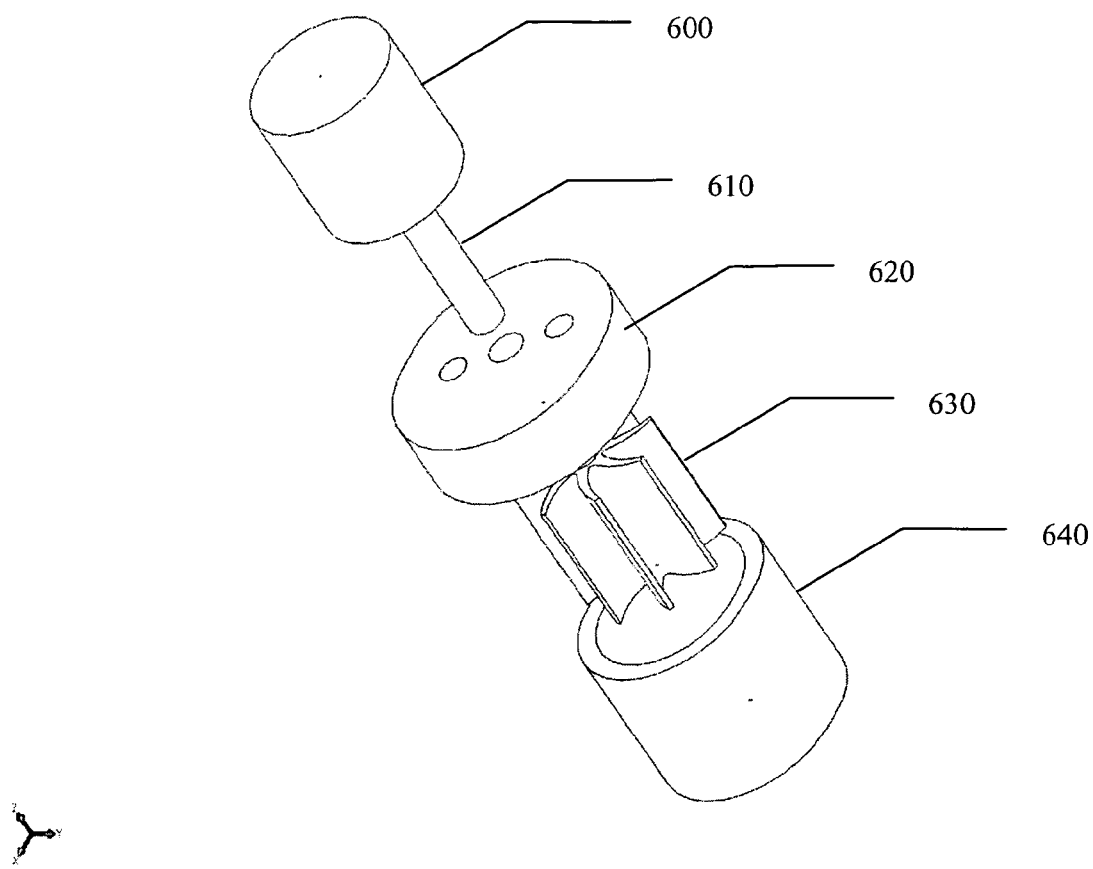
Figure 14: Exploded View of Water Ring Pump
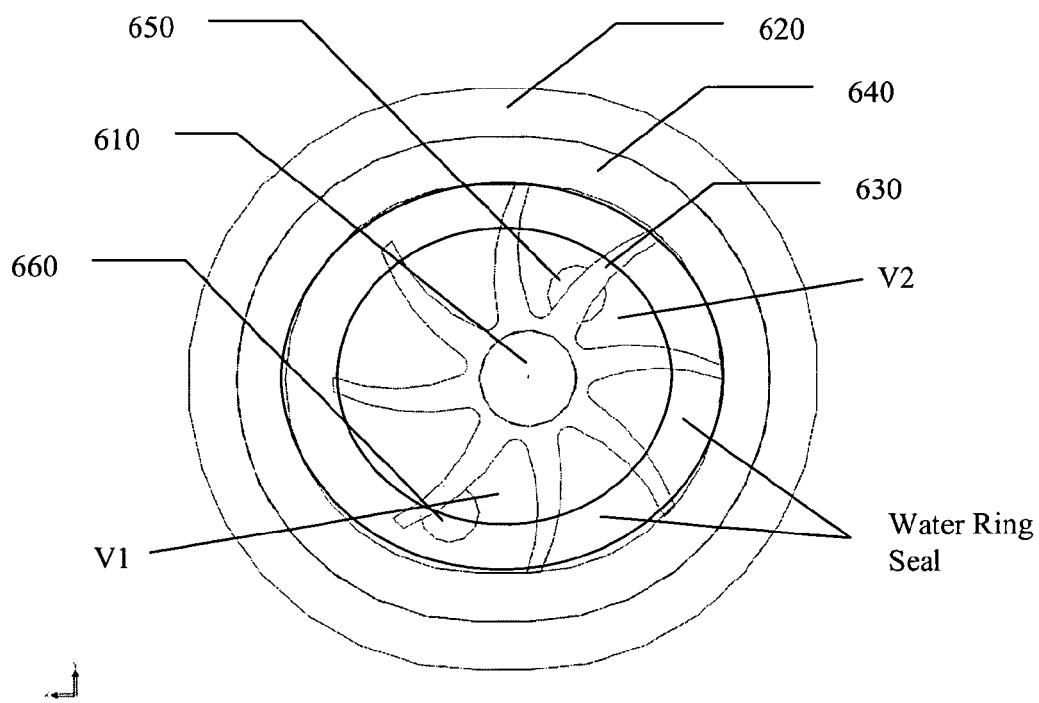
Figure 15: Section View of Water Ring Pump

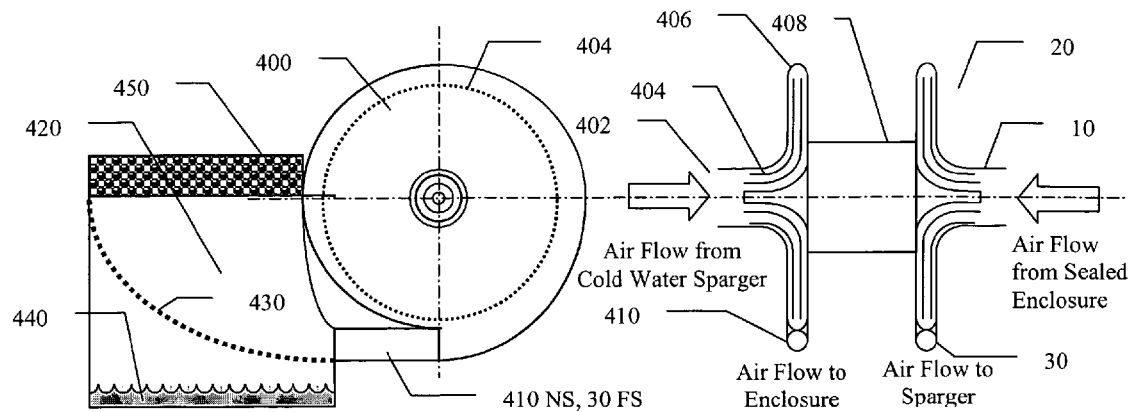
Figure 16: Dual Modified Tesla Turbine Air Pump/Excess Moisture Separator
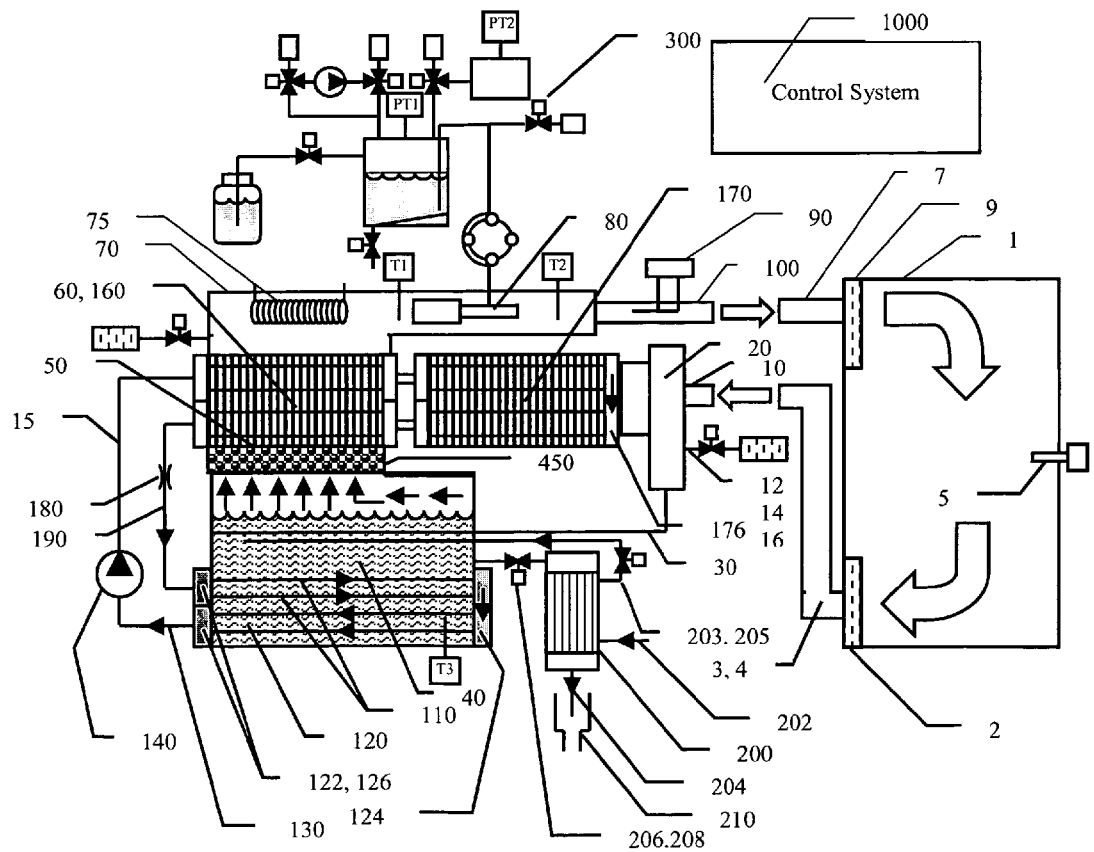
Figure 17: System with Coalescing Element Downstream of Cold Water Bath

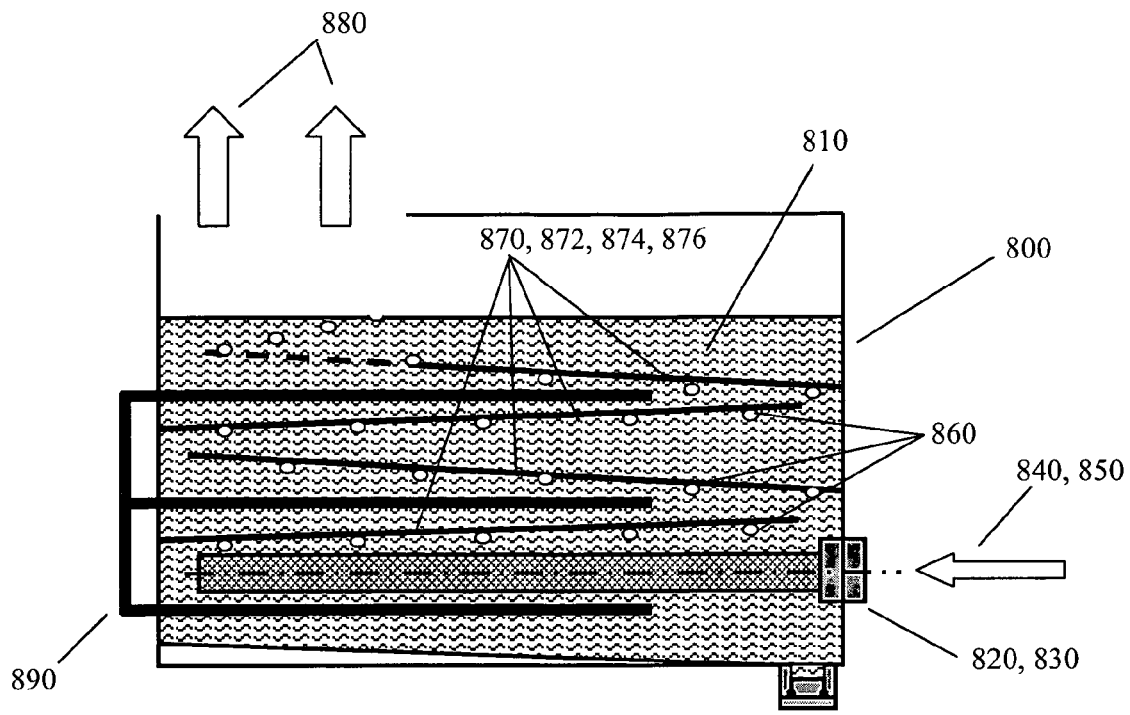
Figure 18(a): Side View of Cold Water Bath
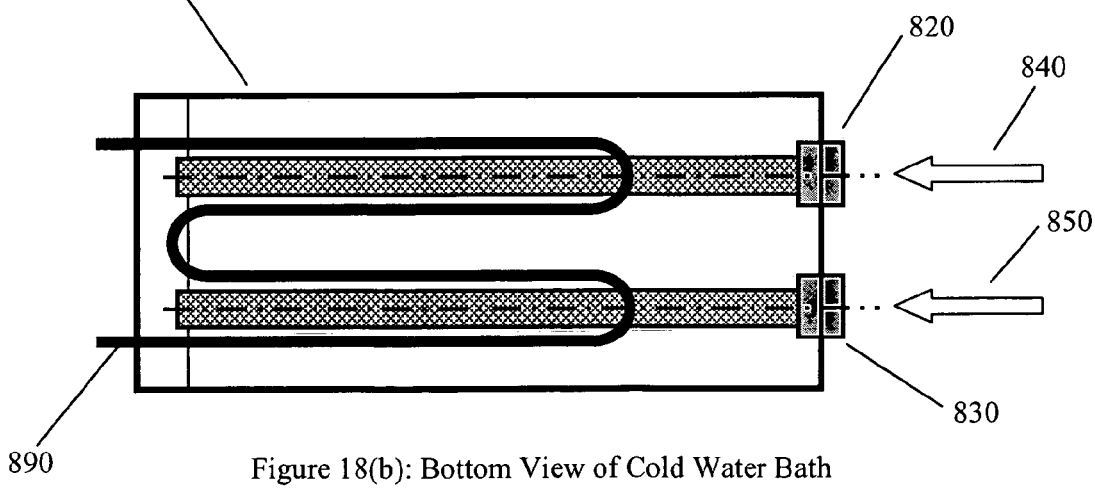
Figure 18(b): Bottom View of Cold Water Bath

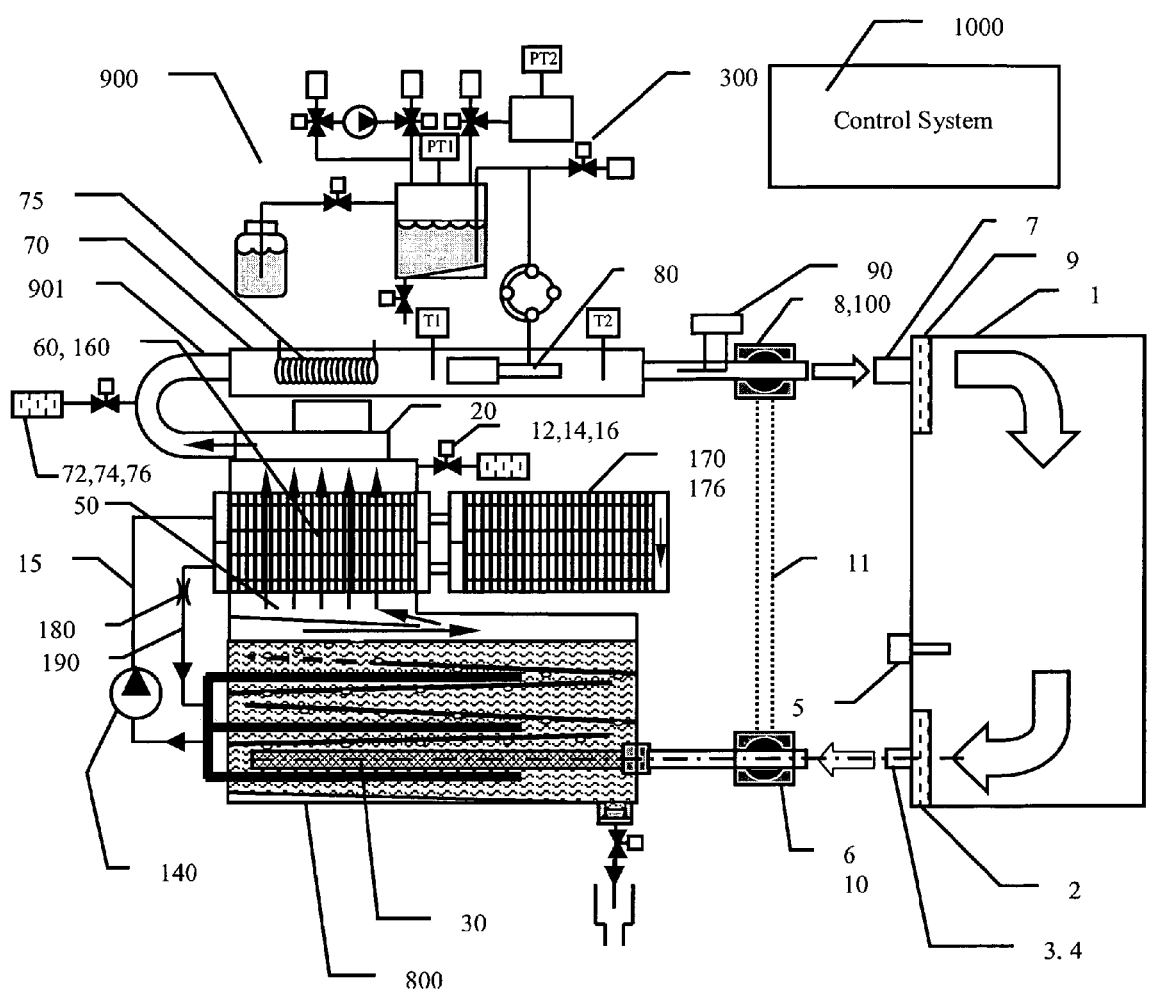
Figure 19: Air Pump Downstream of Water Bath

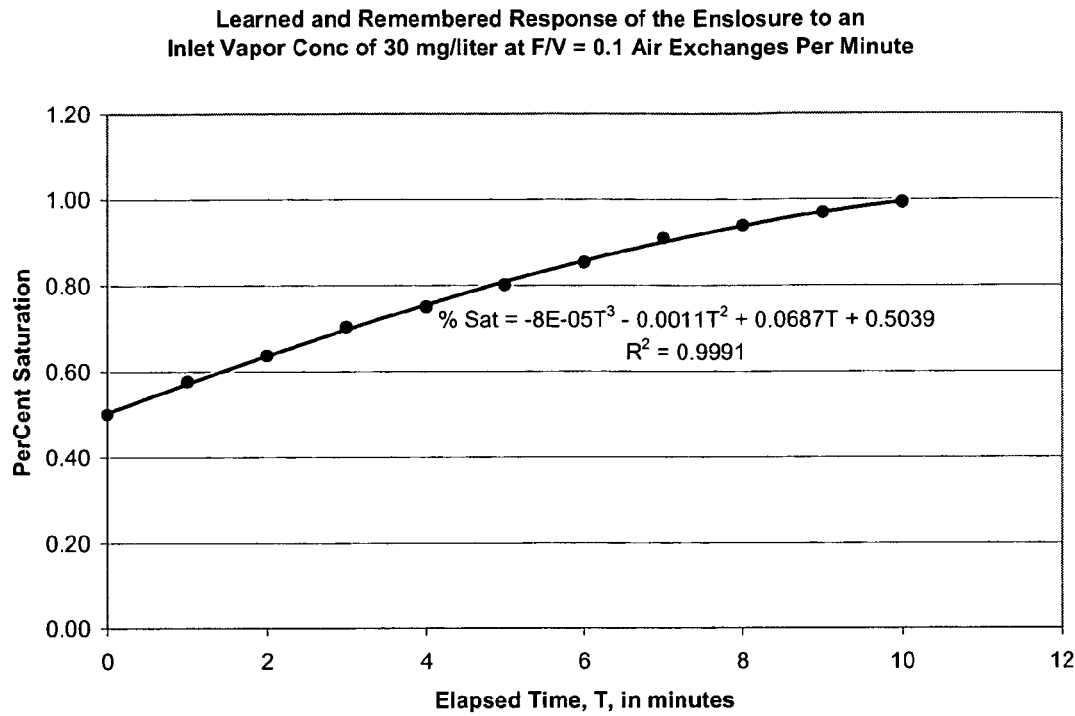
Figure 20: Response of the Enclosure to Inlet Vapor Conc of 30 mg/liter at F/V = 0.1
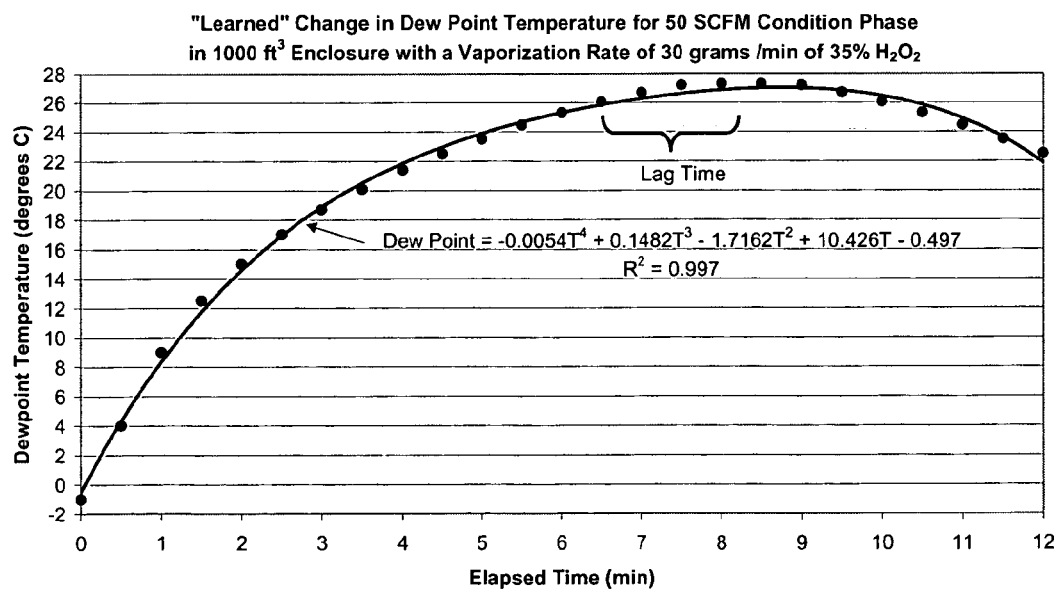
Figure 21: Condition Phase Followed by Aeration Phase

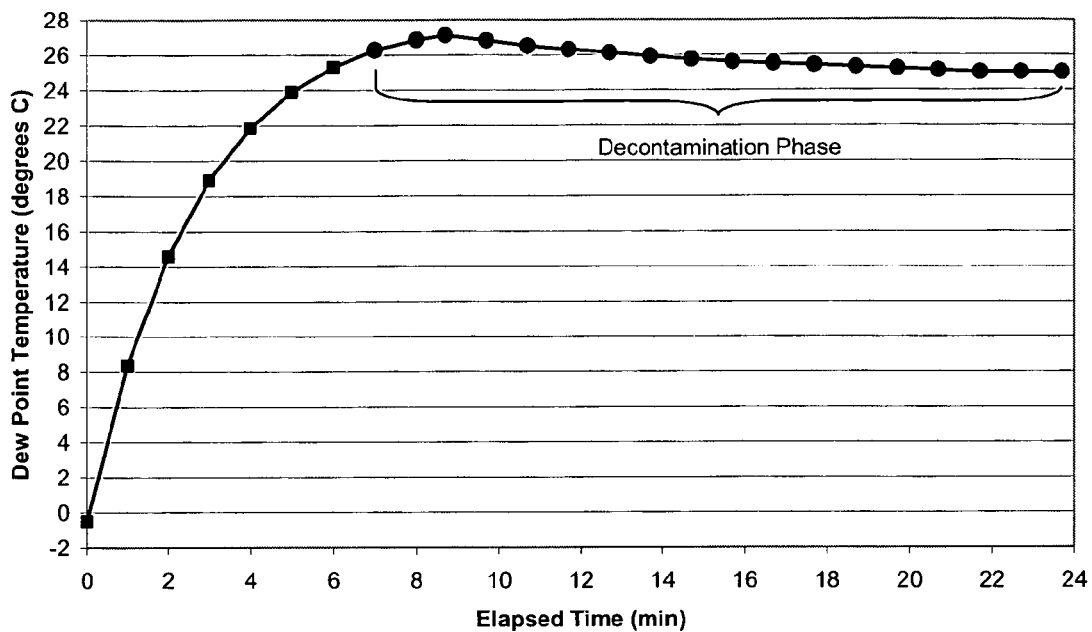
Figure 22: Second Learned Behavior Decontamination Run
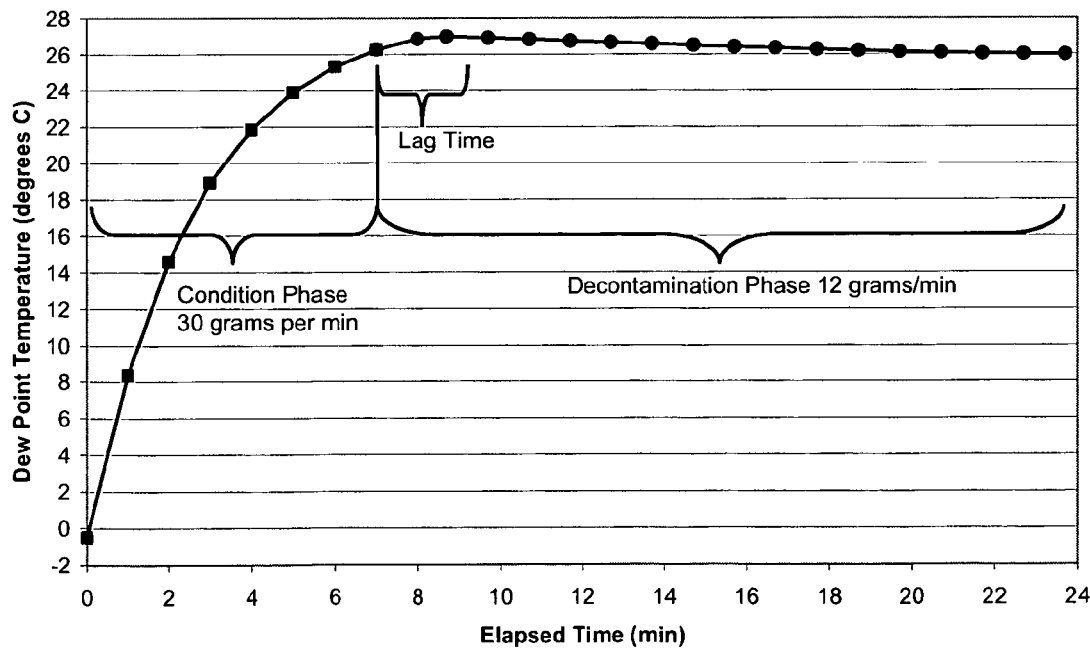
Figure 23: Third Learned Behavior Decontamination Run

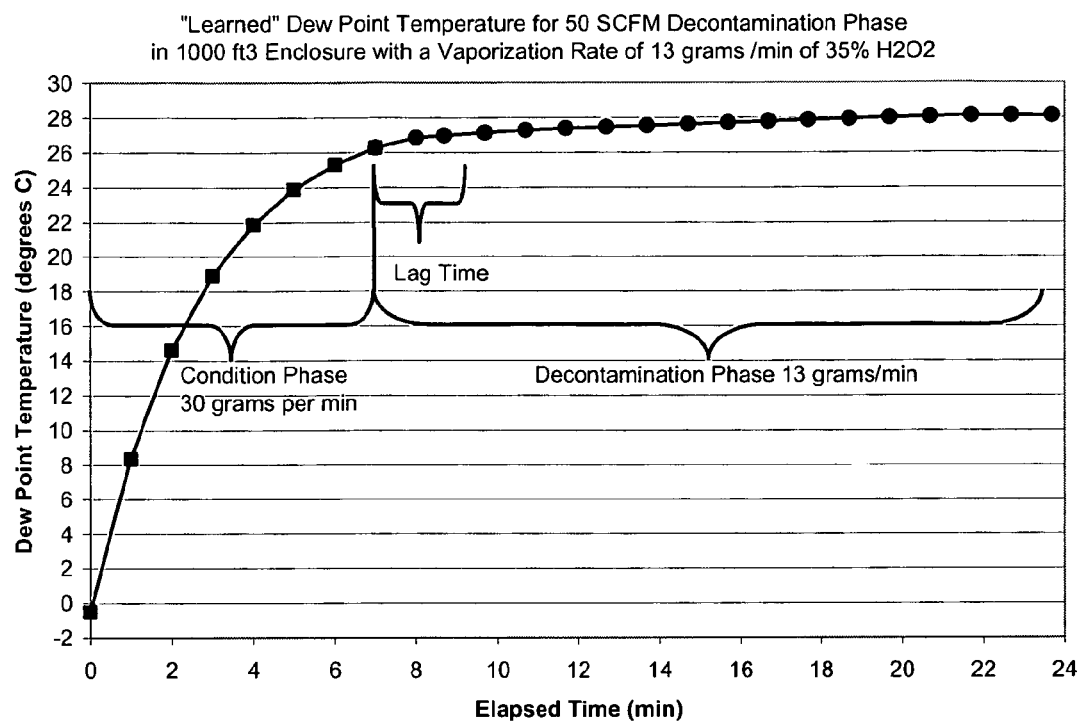
Figure 24: Dew Point Continues to Rise Past the LAG TIME During Decontamination Phase

METHOD AND SYSTEM FOR CONDUCTING VAPOR PHASE DECONTAMINATION OF SEALABLE ENTITIES AND THEIR CONTENTS

PRIORITY CLAIM

This application claims priority to and the benefits as a continuation-in-part application of provisional U.S. patent application "Method and System for Conducting Continuous Operation Flow Vapor Phase Decontamination in either an Open Loop or a Closed Loop", Ser. No. 60/777,072, filed Feb. 25, 2006.

FIELD OF THE INVENTION

The present invention relates generally to a flow-through system and method of vapor-phase decontamination with a multi-component vapor, one component of which is water vapor. The carrier gas flow can be in a single pass, or flow-through mode, or it can be in a multiple-pass, or closed-loop recirculating mode. The entity through which the carrier gas flows can be a sealable enclosure such as an isolator, glove box, clean room, fume hood, safety cabinet, or incubator. The enclosure can also be an object such as a building, an automobile, an ambulance, a military tank, an aircraft, or a ship. The entity can also be a portion on an entity such as a HVAC system in a building, an operating room in a hospital or a patient's room in a hospital or nursing home. The decontamination may be of the entity, the contents of the entity, or both.

BACKGROUND OF THE INVENTION

Sterilization and decontamination of sealable enclosures and their contents has become equally as important today as the sterilization of products and devices. A number of chapters in Aseptic Pharmaceutical Manufacturing II discuss the use of barriers technology in the pharmaceutical industry and the need to decontaminate the interior of the barriers (sealable enclosures). The closed-loop flow-through decontamination systems disclosed in U.S. Pat. No. 5,173,258, U.S. Pat. No. 5,876,664, and U.S. Pat. No. 5,906,794, incorporated by reference herein, are useful for delivering sterilant vapors to sealable enclosures such as glove boxes, biological safety cabinets, the isolators used for sterility testing of pharmaceutical products, pharmaceutical form-fill-seal lines and small clean rooms. The open-loop flow-through decontamination system disclosed in U.S. Pat. No. 4,909,999, incorporated by reference herein, was intended for use with water-jacketed $CO_2$ incubators but could also be used with other sealable enclosures. More recent applications include decontamination of buildings such as post offices U.S. Ser. No. 24/184,950 and decontamination of aircraft U.S. Ser. No. 25/074,359, both incorporated herein by reference.

Improvements are being made continuously in the methods and systems that are used to accomplish flow through sterilization as evidenced by the patents that have been filed in recent years. U.S. Pat. No. 5,445,792 and U.S. Pat. No. 5,508,009, both incorporated by reference herein, disclose a method of maintaining a pre-determined percent saturation by adjusting the rate of hydrogen peroxide injection in response to a predetermined characteristic of the carrier gas. U.S. Pat. No. 5,876,664 and U.S. Pat. No. 5,906,794 disclose a method of controlling both percent saturation and sterilant vapor concentration. U.S. Pat. No. 5,872,359, incorporated by reference herein, discloses a real-time monitor and control system that controls both percent saturation and sterilant vapor concentration.

Sensors that can measure the concentration of the sterilant vapor, typically hydrogen peroxide, in the presence of water vapor are the subjects of a number of issued patents and pending applications including U.S. Ser. No. 56/000,142, U.S. Pat. No. 5,608,156, U.S. Pat. No. 5,847,392, U.S. Pat. No. 5,847,393, U.S. Pat. No. 6,189,368, U.S. Pat. No. 6,269,680, U.S. Pat. No. 6,517,775, U.S. Pat. No. 6,532,794, U.S. Pat. No. 6,537,491, U.S. Pat. No. 6,875,399, U.S. Ser. No. 22/168,289, U.S. Ser. No. 23/021,724, and U.S. Ser. No. 23/115,933, all incorporated herein by reference. Methods to calibrate the sterilant vapor sensors are the subjects of a number of issued patents and pending applications including U.S. Pat. No. 6,581,435, U.S. Pat. No. 6,612,149, U.S. Pat. No. 6,742,378, U.S. Ser. No. 22/152,792, and U.S. Ser. No. 24/016,283, all incorporated herein by reference.

U.S. Pat. No. 5,173,258 discloses the closed loop flow-through system that was commercialized in the highly successful Steris VHP®11000 bio-decontamination system. This system preconditions the air in a sealable enclosure by re-circulating the air through an air dryer until it is at, or below, a pre-determined humidity level. If the air initially has little to no humidity no pre-conditioning is necessary. The air continues to circulate in a closed loop during the decontamination process with vaporized sterilant continuously being generated and mixed with the dehumidified air as it flows into the enclosure. As the partially degraded sterilant and air returns from the enclosure, it passes through a catalytic converter and an air dryer before being heated and combined with vaporized sterilant and returned to the enclosure. The continuous removal of partially degraded sterilant and replacement with freshly generated sterilant maximizes the concentration of the sterilant vapor within the enclosure. However, as the enclosure size increases and the air exchange rate begins to decrease, the system cannot maintain both the vapor concentration and the percent saturation for an extended period of time. FIGS. 5, 6 and 7 in U.S. Pat. No. 5,173,258 illustrate how the allowable concentration decreases with time for lower air exchange rates. FIG. 3 in U.S. Pat. No. 5,906,794 shows how the percent saturation increases with time during a decontamination cycle and can exceed dew point conditions resulting in condensation and a loss of kill efficacy.

The moisture content of the air exiting the air dryer will depend upon the humidity of the air when it enters the air dryer, the air flow rate, the temperature of the air dryer and the remaining capacity of the air dryer. In general, the moisture content of the exit air will increase over time. A steady state for both sterilant vapor concentration and percent saturation cannot be maintained if the rate at which humidity is being removed from the enclosure is not equal to the rate at which water vapor is being introduced into the enclosure. A combination of sterilant vapor sensors, humidity sensors, airflow sensors and temperature sensors used in combination with complex control algorithms cannot control both sterilant vapor concentration and percent saturation for low air exchange rates when the liquid form of the sterilant contains both water and the sterilant because they cannot be introduced independently. Control is further complicated if the sterilant (eg: hydrogen peroxide vapor) degrades into multiple components, one of which is water, during the decontamination process. The best the system can do is to maintain the system at 100% saturation. The combined in-accuracies of the sensors will determine the degree to which the sterilant concentration is monitored and to which the percent saturation is controlled. Redundant, independent sensors may be used in some applications if the failure of a sensor would result in an unacceptable outcome.

The system disclosed in U.S. Pat. No. 5,173,258 requires regeneration when the desiccant capacity has been depleted. The regeneration process is described starting at line 34 in column 8. Regeneration is accomplished by blowing hot air through the desiccant bed to remove the moisture from the bed and discharge it to an outside exhaust. US 2003/0164091 discloses a replaceable desiccant cartridge that could either be discarded after use, or regenerated after use. The cartridge could be removed and regenerated elsewhere as disclosed in the patent application, or an automated switching system could be devised to use one cartridge while another is being regenerated. The system disclosed in U.S. Pat. No. 5,906,794 also uses a desiccant that requires regeneration. A bypass of the air dryer is provided so that the air stream humidity can be controlled to some level that is higher than the output of the air dryer by controlling the amount of air that bypasses the air dryer. A continuously regenerating desiccant wheel could be used with this system as it has a blower on each side of the air dryer. The pressure in the drying portion of the desiccant wheel could be controlled relative to the pressure in the regenerating portion of the wheel minimizing leakage from one side to the other.

All three of the systems mentioned thus far should be able to generate output air streams with humidity levels at, or below, about 30% RH at 25° C. A batch mode system may generate an output air stream with a lower humidity level; however, a continuously operating desiccant system will not be able to do so because the desiccant bed temperature is elevated from the continuous regeneration. The output humidity of the batch mode system will vary over time as the desiccant bed heats up as it absorbs moisture and as the capacity of the bed to remove moisture is depleted. This would present a problem if the batch mode system were to be used as a source of hydrogen peroxide vapor in a steady state environment such as that disclosed in U.S. Pat. No. 5,114,670; U.S. Pat. No. 6,752,959; U.S. Pat. No. 4,742,667 and U.S. Pat. No. 6,752,959; all incorporated herein by reference. The method of the present invention would be able to supply the vapor continuously, at the same vapor concentration level and at the same percent saturation level, and would work well in these applications.

Great Briton patent GB 2308066A, incorporated herein by reference, discloses a dehumidification method beginning with line 7 on page 13 that utilizes a refridgerative air dryer consisting of three heat exchangers. The first heat exchanger cools the air down to around 10° C. The second and third heat exchangers are in parallel. While one is cooled to below freezing and "on line", the other is warmed and "off line". Water is taken out of the air stream as ice by the cold heat exchanger while the "off line" heat exchanger is defrosting. The level of dehumidification is not easy to control with this system as ice is building up on the "on-line" heat exchanger during normal operation and this changes the dynamics of the airflow and the transfer of heat from the air stream.

Table 1 lists the saturation concentration of water vapor for temperatures up to 30° C. The saturation concentration for water vapor at about 5° C. (6.795 mg/liter) is approximately equal to the water vapor content at 30% RH and 25° C. (0.3*23.046=6.91 mg/liter) of the "dry air" produced by the desiccant drying systems. This would suggest that bubbling air through a water bath that is at about 5° C. would produce a stream of air with a humidity that is similar to that exiting the air dryer.

TABLE 1

Water vapor Saturation at Various Temperatures up to 30° C.

| TEMP ° C. | H20 SAT. mg/l | TEMP ° C. | H20 SAT. mg/l | TEMP ° C. | H20 SAT. mg/l |
|---|---|---|---|---|---|
| 0 | 4.847312 | 10 | 9.395863 | 20 | 17.28971 |
| 0.555556 | 5.036285 | 10.55556 | 9.732616 | 20.55556 | 17.86031 |
| 1.111111 | 5.23169 | 11.11111 | 10.07986 | 21.11111 | 18.44859 |
| 1.666667 | 5.433639 | 11.66667 | 10.43781 | 21.66667 | 19.05199 |
| 2.222222 | 5.642449 | 12.22222 | 10.80607 | 22.22222 | 19.672 |
| 2.777778 | 5.858292 | 12.77778 | 11.18639 | 22.77778 | 20.30795 |
| 3.333333 | 6.081361 | 13.33333 | 11.5777 | 23.33333 | 20.96442 |
| 3.888889 | 6.311628 | 13.88889 | 11.98124 | 23.88889 | 21.63841 |
| 4.444444 | 6.549559 | 14.44444 | 12.39662 | 24.44444 | 22.32912 |
| 5 | 6.795449 | 15 | 12.82436 | 25 | 23.04216 |
| 5.555556 | 7.049337 | 15.55556 | 13.26508 | 25.55556 | 23.77399 |
| 6.111111 | 7.311233 | 16.11111 | 13.71952 | 26.11111 | 24.52375 |
| 6.666667 | 7.58184 | 16.66667 | 14.18607 | 26.66667 | 25.29435 |
| 7.222222 | 7.861271 | 17.22222 | 14.66799 | 27.22222 | 26.08519 |
| 7.777778 | 8.149215 | 17.77778 | 15.16225 | 27.77778 | 26.89994 |
| 8.333333 | 8.446566 | 18.33333 | 15.67255 | 28.33333 | 27.73357 |
| 8.888889 | 8.753504 | 18.88889 | 16.19708 | 28.88889 | 28.58989 |
| 9.444444 | 9.069705 | 19.44444 | 16.73518 | 29.44444 | 29.4682 |
| 10 | 9.395863 | 20 | 17.28971 | 30 | 30.36761 |

Chilling the water bath to as low as 0° C. should produce a stream of air with an absolute humidity near 4.84 mg/liter which is equivalent to 21% RH at 25° C. (=100*4.84/23.04216). The humidity of the air stream is automatically decreased, or increased, so that it exits at saturation when it passes through the cold water bath. The desiccant air dryers and the refridgerative air dryers disclosed in the prior art can only reduce the humidity of the air stream. They do not increase it when the air is initially dry. The air dryer bypass 36 in FIG. 6 of U.S. Pat. No. 5,906,794 will also not increase the humidity of the air stream if it is initially dry. Humidity would have to be introduced into the air stream by another method.

Chilling water to 0° C. and maintaining it at 0° C. is fairly easy to do. One calorie of energy is required to reduce the temperature of one gram of water one degree Centigrade. An additional 79.7 calories are required to freeze the water and start to drop the temperature further. Thus, one only needs to cool the water until the temperature stops dropping and it will be at the freezing point.

Assume a continuous recirculating system with a 20 SCFM airflow and a post water bath temperature of 32° F. The recirculating air stream is heated and 6.63 grams per minute of water is vaporized into the air stream resulting in a 95° F. temperature of the moist air stream. The moist air stream flows through a sealed enclosure and back into the water bath where it is cools to 32° F. condensing the entire 6.63 grams per minute of water vapor. The absolute humidity of the 100% saturated air at 32° F. is about 0.1373 grams per cubic foot. The thermal energy required to keep this system operating continuously is estimated in Table 2:

TABLE 2

Energy Requirements

| Step requiring Energy | Energy Calculation | Energy |
|---|---|---|
| Heat 20 SCFM of air from 32° F. to 86° F. | 20 * (86-32) * 0.0771 * 0.24 | 19.98 btu/min |
| Heat 0.1373 grams water vapor/ft$^3$ 32° F. to 86° F. | 20 * (86-32) * 0.1373 * 1/454 | 0.33 btu/min |
| Vaporize 6.63 grams per minute of water | 6.63/454 * 1055 | 15.41 btu/min |
| Cool 20 SCFM of air from 86° F. to 32° F. | 20 * (86-32) * 0.0771 * 0.24 | 19.98 btu/min |
| Cool 0.1373 gram/ft$^3$ from 86° F. to 32° F. | 20 * (86-32) * 0.1373 * 1/454 | 0.33 btu/min |
| Condense 6.63 grams per minute of water | 6.63/454 * 1055 | 15.41 btu/min |
| Total Energy | | 71.44 btu/min = 1.26 KW |

When a refrigeration system is used to cool the water bath, the recirculating air stream can be passed over the condenser coils generating all of the energy required to heat the air from 32° F. to 86° F. reducing the thermal energy requirements to about 0.9 KW. If the air blower is placed downstream of the water bath, the heat generated by the blower will elevate the air temperature further reducing the energy required during the liquid decontaminant injection and vaporization that follows. The Ametek Lamb Infin-A-Tek Model 121001-13 two-stage, peripheral discharge blower specifications are contained in Table 3. About four hundred watts of thermal energy are typically generated and absorbed by the air stream when the blower is operating against a vacuum head ranging from 36 to 80 inches of water column.

TABLE 3

Ametek Lamb Infin-A-Tek Model 121001-13 Blower Performance

| Orifice (Inches) | Amps | Watts | RPM | Vac (In.H2O) | Flow (CFM) | Air Watts |
|---|---|---|---|---|---|---|
| 2 | 13.7 | 1454 | 22640 | 5.6 | 123.6 | 81 |
| 1.75 | 13.7 | 1453 | 22550 | 9.3 | 121.3 | 133 |
| 1.5 | 14 | 1480 | 22470 | 15.4 | 113.1 | 205 |
| 1.25 | 14.1 | 1543 | 22430 | 27 | 104 | 330 |
| 1.125 | 14.1 | 1538 | 22350 | 35.6 | 96.4 | 404 |
| 1 | 14.1 | 1538 | 22350 | 45.8 | 86 | 463 |
| 0.875 | 13.9 | 1525 | 22500 | 57.1 | 73.4 | 493 |
| 0.75 | 13.5 | 1436 | 22780 | 67.8 | 58.5 | 467 |
| 0.625 | 12.9 | 1358 | 23380 | 78.6 | 43.6 | 403 |
| 0.5 | 11.4 | 1209 | 24110 | 87.6 | 29.4 | 303 |
| 0.375 | 10.3 | 1097 | 25240 | 97 | 17.3 | 198 |
| 0.25 | 10.1 | 1055 | 27000 | 109.3 | 8.4 | 108 |
| 0 | 9.1 | 963 | 27750 | 120.3 | 0 | 0 |

The freezing point of water can be depressed to below 0° C. by adding solutes to the water. The website http://chemistry.about.com/cs/howthingswork/a/aa120703a.htm contains a list of chemicals that melt ice by lowering depressing the freezing point. This list is duplicated in Table 4. When solutes are added, the freezing point will be depressed; however, the temperature will stop falling at the freezing point until sufficient energy has been removed to freeze all of the solution so it is still easy to identify the freezing point.

TABLE 4

Chemicals that Depress the Freezing Point of Water

| Name | Formula | Lowest Practical Temp | Pros | Cons |
|---|---|---|---|---|
| Ammonium sulfate | (NH4)2SO4 | −7° C. (20° F.) | Fertilizer | Damages concrete |
| Calcium chloride | CaCl2 | −29° C. (−20° F.) | Melts ice faster than sodium chloride | Attracts moisture, surfaces are slippery below −18° C. (0° F.) |
| Calcium magnesium acetate (CMA) | Calcium carbonate CaCO3, magnesium carbonate MgCO3, and acetic acid CH3COOH | −9° C. (15° F.) | Safest for concrete & vegetation | Works better to prevent re-icing than as ice remover |
| Magnesium chloride | MgCl2 | −15° C. (5° F.) | Melts ice faster than sodium chloride | Attracts moisture |
| Potassium acetate | CH3COOK | −9° C. (15° F.) | Biodegradable | Corrosive |
| Potassium chloride | KCl | −7° C. (20° F.) | Fertilizer | Damages concrete |
| Sodium chloride (rock salt, halite | NaCl | −9° C. (15° F.) | Keeps sidewalks dry | Corrosive, damages concrete & vegetation |

TABLE 4-continued

| Chemicals that Depress the Freezing Point of Water | | | | |
|---|---|---|---|---|
| Name | Formula | Lowest Practical Temp | Pros | Cons |
| Urea | NH2CONH2 | −7° C. (20° F.) | Fertilizer | Agricultural grade is corrosive |

A pleasant application of the freezing point depression is in the making of homemade ice cream. The ice cream mix is put into a metal container that is surrounded by crushed ice. Then salt is put on the ice to lower its melting point. The melting of the solution tends to lower the equilibrium temperature of the ice/water solution to the melting point of the solution. This gives a temperature gradient across the metal container into the saltwater-ice solution which is lower than 0° C. The heat transfer out of the ice cream mix allows it to freeze.

A visit to the DOW Chemical website produced FIG. 1 and Table 5 for calcium chloride. The data in table 4 assume a solution temperature of 77° F. (25°). A calcium chloride solution will allow the water to remain in the liquid state at temperatures well below the normal freezing point of water. The concentration of calcium chloride mixture will determine the new freezing point.

The method of the invention bubbles air through a sparger into a cold-water bath to humidify (precondition) the air before sterilant vapors are introduced. The result is a continuous operation decontamination system that can operate reliably with fewer, less expensive sensors while maximizing both sterilant concentration and percent saturation The design of the sparger that is located within the water bath should be such that it maximizes the surface to volume ratio of the air bubbles that are passing through the cold-water bath. It should also limit the velocity of the air bubbles in order to provide sufficient contact time between the air bubbles and the cold-water bath. The air stream can also be passed through a heat exchanger that will cool the air stream before it enters the sparger.

TABLE 5

| Freezing Point Depression for Calcium Chloride and Water Solutions | | | | | | | | |
|---|---|---|---|---|---|---|---|---|
| % $CaCl_2$ | Approx Specific Gravity | Weight in lb/gal (kg/liter) | Gal/Ton (l/metric ton) of solution | Gal/dry ton (l/dry metric ton) | DowFlake 77-80% $CaCl_2$ Equiv in lb/gal or (kg/l) of sol | PelaDow 90-92% $CaCl_2$ Equiv in lb/gal or (kg/l) of sol | Annhydrous 94-97% $CaCl_2$ Pellets Equiv in lb/gal or (kg/l) of sol | Approx Freezing Point deg F. (deg C.) |
| 0 | 1 | 8.31 (0.997) | NA | NA | NA | NA | NA | +32 (0) |
| 10 | 1.09 | 9.06 (1.087) | 221 (920) | 2,208 (9,200) | 1.16 (0.139) | 1.00 (0.119) | 0.96 (0.114) | +20 (−7) |
| 11 | 1.1 | 9.14 (1.097) | 219 (912) | 1,989 (8,287) | 1.29 (0.155) | 1.10 (0.133) | 1.06 (0.127) | +18 (−8) |
| 12 | 1.11 | 9.22 (1.107) | 217 (903) | 1,808 (7,528) | 1.42 (0.170) | 1.22 (0.146) | 1.16 (0.140) | +16 (−9) |
| 13 | 1.12 | 9.31 (1.117) | 215 (895) | 1,653 (6,887) | 1.55 (0.186) | 1.33 (0.160) | 1.27 (0.153) | +14 (−10) |
| 14 | 1.129 | 9.38 (1.126) | 213 (888) | 1,523 (6,334) | 1.68 (0.202) | 1.44 (0.173) | 1.38 (0.166) | +12 (−11) |
| 15 | 1.139 | 9.47 (1.136) | 211 (880) | 1,408 (5,869) | 1.82 (0.218) | 1.56 (0.187) | 1.50 (0.179) | +10 (−12) |
| 16 | 1.149 | 9.55 (1.146) | 209 (873) | 1,309 (5,454) | 1.96 (0.235) | 1.68 (0.201) | 1.61 (0.193) | +8 (−13) |
| 17 | 1.159 | 9.63 (1.156) | 208 (865) | 1,222 (5,089) | 2.10 (0.252) | 1.80 (0.216) | 1.72 (0.207) | +5 (−15) |
| 18 | 1.169 | 9.71 (1.165) | 206 (858) | 1,144 (4,769) | 2.24 (0.269) | 1.92 (0.231) | 1.84 (0.221) | +2 (−17) |
| 19 | 1.179 | 9.80 (1.175) | 204 (851) | 1,074 (4,479) | 2.39 (0.286) | 2.05 (0.245) | 1.96 (0.235) | −1 (−18) |
| 20 | 1.189 | 9.88 (1.185) | 202 (844) | 1,012 (4,219) | 2.53 (0.304) | 2.17 (0.261) | 2.08 (0.250) | −4 (−20) |
| 21 | 1.199 | 9.96 (1.195) | 201 (837) | 956 (3,985) | 2.68 (0.322) | 2.30 (0.276) | 2.20 (0.264) | −8 (−22) |
| 22 | 1.209 | 10.05 (1.205) | 199 (830) | 905 (3,772) | 2.83 (0.340) | 2.43 (0.291) | 2.33 (0.279) | −12 (−24) |
| 23 | 1.219 | 10.13 (1.215) | 197 (823) | 858 (3,578) | 2.99 (0.358) | 2.56 (0.307) | 2.45 (0.294) | −16 (−27) |
| 24 | 1.228 | 10.20 (1.224) | 196 (817) | 817 (3,404) | 3.14 (0.377) | 2.69 (0.323) | 2.58 (0.309) | −20 (−29) |
| 25 | 1.24 | 10.30 (1.236) | 194 (809) | 777 (3,236) | 3.30 (0.396) | 2.83 (0.340) | 2.71 (0.325) | −25 (−32) |
| 26 | 1.251 | 10.40 (1.247) | 192 (802) | 740 (3,084) | 3.47 (0.416) | 2.97 (0.356) | 2.85 (0.341) | −31 (−35) |
| 27 | 1.263 | 10.50 (1.259) | 190 (794) | 706 (2,942) | 3.63 (0.436) | 3.12 (0.374) | 2.98 (0.358) | −38 (−39) |
| 28 | 1.275 | 10.60 (1.271) | 189 (787) | 674 (2,810) | 3.81 (0.456) | 3.26 (0.391) | 3.12 (0.375) | −46 (−43) |
| 29 | 1.287 | 10.69 (1.283) | 187 (779) | 654 (2,688) | 3.97 (0.477) | 3.41 (0.409) | 3.26 (0.392) | −53 (−47) |
| 29 | 1.294 | 10.75 (1.290) | 186 (775)) | 629 (2,619 | 4.08 (0.490) | 3.50 (0.420) | 3.35 (0.402) | −60 (−51) |
| 30 | 1.298 | 10.79 (1.294) | 185 (773) | 618 (2,578) | 4.15 (0.498) | 3.56 (0.427) | 3.41 (0.409) | −52 (−47) |
| 31 | 1.31 | 10.89 (1.306) | 184 (766) | 592 (2,470) | 4.33 (0.519) | 3.71 (0.445) | 3.55 (0.426) | −34 (−37) |
| 32 | 1.322 | 10.99 (1.318) | 182 (759) | 569 (2,371) | 4.51 (0.541) | 3.86 (0.463) | 3.70 (0.444) | −17 (−27) |
| 33 | 1.334 | 11.09 (1.330) | 180 (752) | 547 (2,278) | 4.69 (0.563) | 4.02 (0.482) | 3.85 (0.462) | −4 (−20) |
| 34 | 1.345 | 11.18 (1.341) | 179 (746) | 526 (2,193) | 4.87 (0.585) | 4.18 (0.501) | 4.00 (0.480) | +10 (−12) |
| 35 | 1.357 | 11.28 (1.353) | 177 (739) | 507 (2,112) | 5.06 (0.607) | 4.34 (0.520) | 4.16 (0.498) | +20 (−7) |
| 36 | 1.369 | 11.38 (1.365) | 176 (733) | 488 (2,035) | 5.25 (0.630) | 4.50 (0.540) | 4.31 (0.517) | +30 (−1) |
| 37 | 1.381 | 11.48 (1.377) | 174 (726) | 471 (1,963) | 5.45 (0.653) | 4.67 (0.560) | 4.47 (0.536) | +39 (+4) |
| 38 | 1.392 | 11.57 (1.388) | 173 (720) | 455 (1,891) | 5.64 (0.676) | 4.83 (0.580) | 4.63 (0.555) | +48 (+9) |
| 39 | 1.404 | 11.67 (1.400) | 171 (714) | 439 (1,832) | 5.84 (0.700) | 5.00 (0.600) | 4.79 (0.575) | +55 (+13) |
| 40 | 1.416 | 11.77 (1.412) | 170 (708) | 425 (1,771) | 6.04 (0.724) | 5.17 (0.621) | 4.96 (0.594) | +61 (+16) |
| 41 | 1.428 | 11.87 (1.424) | 168 (702) | 411 (1,713) | 6.24 (0.748) | 5.35 (0.631) | 5.12 (0.614) | +65 (+18) |
| 42 | 1.439 | 11.96 (1.435) | 167 (697) | 398 (1,659) | 6.44 (0.773) | 5.52 (0.662) | 5.29 (0.634) | +69 (+21) |
| 45 | 1.474 | 12.25 (1.470) | 163 (680 | 363 (1,512) | 7.07 (0.848) | 6.06 (0.727) | 5.80 (0.696) | +78 (+26) |

The surface to volume ratio for a spherical bubble of radius R can be calculated from the equation for the surface area of a sphere and the equation for the volume of a sphere.

$$\text{Surface Area of Sphere} = 4Pi*R^2$$

$$\text{Volume of a Sphere} = 4Pi*R^3/3$$

$$\text{Surface/Volume} = \frac{4Pi*R^2}{4Pi*R^3/3} = 3R$$

Thus, the smaller the radius, the higher is the surface to volume ratio of the of the spherical air bubble. A sintered metal sparger would generate much smaller air bubbles when compared to a sparger made by punching or drilling holes in a metal tube or plate. Mott Corporation of Farmington, Conn. has a complete product line of sintered metal spargers. The size of the sparger that is required in an application will be dependent upon the carrier air flow rates as this will determine the velocity of the air bubbles as they exit the sparger and will affect time the air stream has in contact with the cold water bath.

It may be advantageous to place a coalescing filter downstream of the water bath (refer to FIG. 17) so that any excess moister that may be entrained within the cold air stream has a surface upon which it can collect and drip back into the water bath. Sintered metal may be able to be used for this coalescing filter.

Centrifugal force can also be used to separate any excess moisture that is entrained in the air stream that is exiting the cold-water bath. The Modified Tesla turbine air pump is well suited to this purpose. A single, or a dual, modified Tesla turbine could push the carrier air flow into the sparger and withdraw it from the cold water bath, separating out excess moisture (refer to FIG. 16). As the air exits the modified Tesla turbine at a high velocity, the excess moisture is thrown to the outside of the blower by centrifugal force. As the air enters an expansion chamber and slows down, the excess moisture accumulates on the sloped, perforated air guide and drips into an accumulation chamber. The carrier airflow continues through the coalescing filter. Moisture that gathers on the coalescing filter can also drip into the accumulation chamber.

SUMMARY OF THE INVENTION

The present invention provides a method of performing a continuous flow through vapor phase decontamination in either a closed loop or an open loop. The invention can accommodate a wide range of airflow rates.

The method of the invention will be described in the closed loop, continuous flow mode of operation as this is the preferred mode. In the method, a flow of carrier gas is recirculated in a closed loop conduit circuit that leads into, through, and out of a sealable enclosure. The invention can be used for airflow rates ranging from less than one SCFM to thousands of SCFM.

In a preferred embodiment, air is drawn from the sealed enclosure during the humidification, conditioning, decontamination and aeration phases and into an inlet line by an air pump, or blower, that is able to generate a maximum flow that is at least ten times the minimum flow rate. The air pump discharges the air into a sparger that is submerged in an ice cold water bath. The air stream is broken into small bubbles by the sparger. If the incoming air is humid, excess moisture in the bubbles condenses into the water bath so that the air bubbles exit saturated with water vapor based upon the ice-cold temperature of the water bath. If the incoming air is dry, the air bubbles pick up water vapor from the water bath and exit saturated with water vapor based upon the ice-cold temperature of the water bath.

The cold, humidified air stream passes through the condenser of a refrigeration system after exiting the water bath warming the humidified air stream. The compressed refrigerant in the condenser later expands into an evaporator coil that is used to cool the cold-water bath.

In an alternative, low cost embodiment, ice could be placed in the water bath at the beginning of a decontamination process, to maintain the temperature of the water bath at the freezing point. Ice could be added manually, or automatically, during the decontamination process if needed. This would eliminate the need for the system to have a refrigeration system.

The air stream next passes over an in line heater that warms the air stream. The air stream is brought up to room temperature during the humidification and aeration phase and to the pre-injection temperature during the condition and decontamination phases. Atomized liquid sterilant is mixed with the heated airflow during the condition and decontamination phases.

The liquid sterilant can be atomized by any known means. Known atomizing means would include fluid pressure nozzles, pressurized air nozzles, ultrasonic atomizer nozzles, and piezo-electric atomizers. Ultra-sonic nozzles such as those manufactured by Sonics, Sonotek, Lechler and Sonicom can be used with peristaltic fluid metering pumps and are preferred as they produce fine mists using low pressures and they can be made of materials that do not degrade the liquid sterilant during the atomization process. Atomization and the conversion to vapor by heat transfer from the air stream are preferred, as residues do not build up on the vaporizer surfaces. U.S. Pat. No. 5,258,162, incorporated herein by reference, discloses a method wherein vaporization of finely-divided liquid hydrogen peroxide is accomplished by an air current at a constant, elevated vaporization temperature. U.S. Pat. No. 4,742,667, incorporated herein by reference, discloses the use of compressed air to convert the liquid sterilant into fine droplets that impinge on the interior surfaces of a heated tube.

The flow from peristaltic metering pumps will not increase linearly with pump rotational speed because of a number of factors including, but not limited to, pump inlet pressure, pump outlet pressure, fluid temperature, and the time the tubing has to go from the pump roller flattened state to its near round shape as it draws in fluid. Some systems, such as that disclosed in U.S. Pat. No. 5,173,258, place the reservoir from which the peristaltic pump withdraws liquid sterilant on an electronic balance and use feedback from the electronic balance to adjust the pump speed to produce the desired sterilant flow and vaporization rate. US 2004/0191112 discloses a closed loop fluid metering system that is based upon the rotational speed of the pump. This system would not require the expensive electronic balance like the system disclosed in U.S. Pat. No. 5,173,258; however, it would be expected to result in more variation in sterilant flow rate and the vaporization rate based upon the data contained in FIGS. 2 and 3. The actual output flow differed from the nominal flow rate by 20% to −40% as the inlet pressure fell from +700 mm Hg to −260 mm Hg. FIG. 4 shows that the outlet back pressure does not have much of an affect on the outlet flow rate.

Thus, there is a need for a liquid decontaminant pumping system with a cost comparable to the system disclosed in US 2004/0191112 but with the performance of the more expensive system disclosed in U.S. Pat. No. 5,173,258.

The present invention includes such a system. The closed loop feedback system consists of two reservoirs, one of which is partially filled with liquid sterilant and the second that is only filled with air. The volume of each reservoir is known. The volume of fluid in the sterilant supply reservoir can be measured at any time using a six-step process.

1. Pressurizing the sterilant reservoir with unknown air volume V1 air to pressure P1 and the air reservoir with known volume V2 to pressure P2 with air.
2. Measure and record the pressures in each reservoir.
3. Open a valve so that the pressure in the two reservoirs equilibrates to pressures P1' and P2'.
4. Measure and record the pressure in each of the reservoirs.
5. Calculate the volume of air in the sterilant reservoir using the following equation:

$$V1air = \frac{P2' - P2}{P1 - P1'} * V2 \qquad \text{Equation 1(a)}$$

6. Subtract the volume of air in the sterilant reservoir from the total sterilant reservoir volume to determine the volume of fluid in the reservoir.

$$V2 \text{liquid sterilant} = V2\text{total} - V2\text{air} \qquad \text{Equation 2}$$

Equations 1(a) and 2 are derived from the ideal gas law $P*V=n*R*T$ and are valid as long as the temperature of the air is the same in both reservoirs during both sets of pressure measurements. If the temperature is not the same, the equations are more complicated and temperature measurements are required. Equation 1(b) is substituted for equation 1(a) when the temperature of the air is not the same in both reservoirs during both sets of pressure measurements.

$$V1air = \frac{T1*T1'}{T2*T2'} * \frac{P2'*T2 - P2*T2'}{P1*T1' - P1'*T1} * V2 \qquad \text{Equation 1(b)}$$

The rate are which liquid sterilant is exiting the reservoir can be monitored on a real time basis once the air volume is known in the sterilant reservoir. If the initial volume of air in the reservoir is Vinitial and the pressure is Pinitial, then the volume of air in the reservoir at any time increment thereafter can be calculated using equation 3.

$$Vair \text{ at time } T = \frac{P\text{initial}}{P \text{ at time } T} * V\text{initial} \qquad \text{Equation 3}$$

The volume of liquid sterilant that has been atomized and vaporized in any given time interval is calculated by subtracting the air volume at the beginning of the time interval from the air volume at the end of the time interval. The sterilant flow and vaporization rate is the volume atomized in the time interval divided by the length of the time interval.

This method provides flow rate feedback that can be used to increase the pump speed as the liquid level in the reservoir falls. Otherwise, when the reservoir level fell, the pump inlet head would have decreased and the pump flow rate would have decreased.

The air pump can also generate a vacuum that can be used to draw liquid sterilant from another source to replenish the sterilant in the reservoir eliminating the need for a replenish pumping circuit. The vacuum replenish circuit is simple and inexpensive; furthermore, it does trap any liquid sterilant that could degrade and pressurize the lines in the replenish circuit.

An air flow meter is used to monitor and control the rate at which the air is withdrawn from the sealed enclosure and circulated through the system. Pressure sensors are used to monitor and control the pressure in the sealed enclosure. Air is added to the system if the sealed enclosure pressure falls, and air is removed from the system in the sealed enclosure pressure rises. A valve and HEPA (High Efficiency Particulate Air) filter is placed at an appropriate point in the air flow path that is always under negative pressure so that air can be added to the system by opening the valve. Another valve and HEPA (High Efficiency Particulate Air) filter is placed at an appropriate point in the air flow path that is always under positive pressure so that air can be removed from the system by opening the valve.

The system needs only one blower to remove air from the sealed enclosure and return it to the sealed enclosure because the system is sealed except for the two valves that can add or discharge air based upon the pressure in the sealed enclosure. The blower can be of any know type that is capable of generating the required flow rates and pressures as long as it can stand up to exposure to the sterilant vapor. Acceptable blowers include regenerative blowers, centrifugal blowers, vane pumps, lobe pumps, screw pumps, scroll pumps, diaphragm pumps, piston pumps, velocity impellers (Tesla Turbines), and water ring pumps. U.S. Pat. No. 4,402,647, incorporated herein by reference, discloses a velocity impeller design. A velocity impellers output (pressure and flow) increases with speed so it can produce a wide range of flows against back-pressures that would stall many conventional blowers. Water ring pumps are capable of creating large pressure differentials when they are used as roughing pumps for roots blowers in freeze drying applications so they should have no problem when used in a flow through decontamination system. Smaller, lighter water ring pumps with lower compression ratios would be ideal for use in the method of the invention since cold water is already being used in the system. The water ring pump would assist in mixing the vapors with the cold water so that the exiting air stream would be very close to the natural vapor equilibrium with the cold water in the sparger.

The system does not require a catalytic converter to break down the sterilant, preferably hydrogen peroxide, vapors into water vapor and oxygen. The sterilant vapors condense more readily than the water vapor when the air stream passes through the cold-water bath. The dilute, liquid sterilant can be discharged to the drain along with water, or it can be allowed to break down in the water bath if the water bath is constructed of materials such as stainless steel that are somewhat catalytic to the breakdown reaction. The residual concentrations of sterilant in the cold-water bath will prevent bacteria, fungus, or molds from growing in the system.

The concentration of $H_2O_2$ vapor that will go into the flowing air stream as it passes through the cold-water bath when it contains a low concentration of liquid hydrogen peroxide will be well below 1 ppm. The concentration of $H_2O_2$ vapor that would go into the flowing air stream as it passes through a 0.1 mole fraction solution of hydrogen peroxide can be estimated from Tables 17 and 18 on pages 226 and 227 of Hydrogen Peroxide by Walter C. Schumb, incorporated herein by reference. The total vapor pressure above 0.1 mole fraction solution is 4.06 mm Hg and the mole fraction of the vapor that is hydrogen peroxide is only 0.002. Thus, the concentration of $H_2O_2$ vapor in parts per million (ppm) introduced into an air stream passing through a 0.1 mole fraction hydrogen peroxide solution can be estimated as follows:

$$ppm = \frac{4.06 \text{ mm Hg } (H_2O_2 + H_2O)}{60 \text{ mm Hg } (Air + H_2O_2 + H_2O)} *$$

$$0.002 \text{ mole fraction } H_2O_2 \text{ in vapor} * 10^6 = 10.5 \text{ ppm}$$

A 0.1 mole fraction solution is equivalent to a 17.3% by weight hydrogen peroxide solution. Since the hydrogen peroxide solution in the water bath will be well below 1% by weight, the concentration in the flowing air stream exiting the cold-water bath should be well below 1 ppm.

The method of the invention will maintain the concentration of hydrogen peroxide vapor at its maximum by controlling the air stream flow rate and the pre-injection humidity of the air stream. The amount of liquid sterilant that is atomized and introduced into the heated air stream, where it then vaporizes, will be controlled based upon the percent saturation of the sterilant laden air stream that is returning to the system from the sealed enclosure.

The amount of $H_2O_2$ vapor that cane be present along with $H_2O$ vapor at various temperatures can be obtained from Table II of U.S. Pat. No. 4,956,145, incorporated herein by reference, or it can calculated using the following basic program. Percent saturation is the ratio of the actual $H_2O_2$ vapor concentration divided by the maximum allowable $H_2O_2$ vapor concentration under the given conditions.

```
REM PROGRAM TO CALCULATE H2O2VAPOR CHARACTERISTIC F0R 1 TO 89% H2O2
REM BASED UPON THE METHOD DISCLOSED IN US PATENT 4,956,145
DIM YH(100), PTOTAL(100), PRISE(100, 100), WT(100, 100)
COMMON N, RITE2, PRISE, WT
COMMON A0, A1, A2, A3, A4, A5, A6, R, B0, B1, B2, T
REM METHOD USED TO OBTAIN CONSTANTS A0 THROUGH A6 MAY HAVE VARIED
REM AND MAY ACCOUNT FOR DIFFERENCES BETWEEN CUMMINGS, GAGNE AND
CHILDERS
LET A0 = 4.5767
LET A1 = .33802
LET A2 = .009989
LET A3 = 2.4015E-04
LET A4 = 1.1403E-06
LET A5 = 3.0332E-08
LET A6 = -3.5945E-11
LET R = 1.986
REM 82.1 ml atm/mole K, 62.3 liter mm Hg/mole K = R1
LET R1 = 83.14 / 1.3345
REM GAS CONSTANT DEFINED
PRINT "ENTER THE PERCENT H2O2 BY WEIGHT ="
INPUT PERCENT
PERCENT = PERCENT / 100
LET XH = (18.015 / (34.015 / PERCENT - 15.9994))
LET XW = 1 - XH
LET XW2 = XW
LET XH2 = XH
REM CALCULATE FOR TEMPERATURE FROM 0 TO 100C
FOR I = 0 TO 100 STEP 5
LET T = I
LET B0 = -752 + .97 * T
LET B1 = 85
LET B2 = 13
GOSUB 50
LET YH(I) = YHCALC
LET PTOTAL(I) = PTOT
NEXT I
1    REM CONTINUE
GOSUB 60
REM ASSUME FLASH VAPORIZATION IS UTILIZED
REM USE POLYNOMIAL AT 50C FOR 1ST ESTIMATE
REM CALCULATE MAXIMUM H2O2 THAT CAN BE FLASHED
LET C0 = .14495
LET C1 = 4.1606
LET C2 = -9.3985
LET C3 = 7.2227
LET C4 = 0
LET C5 = 0
LET C6 = 0
FOR J = 5 TO 95 STEP 5
     LET PERCENT = PERCENT * 100
     LET RH = J / 100
     FOR I = 0 TO 100 STEP 1
     REM XH2 IS THE FIRST ESTIMATE OF THE LIQUID PERCENTAGE
     LET XH2=C0+C1*XH+C2*XH^2+C3*XH^3+C4*XH^4+C5*XH^5+C6*XH^6
2    REM CONTINUE
     LET XW2 = 1 - XH2
     T = I
     GOSUB 50
     LET PW = PW * RH
5    LET YH = (PTOT - PW) * XH / PTOT
     LET DELTA = YHCALC - YH
     IF ABS(DELTA) <= .0005 THEN 20
```

```
      REM ADJUST LIQUID PERCENT TO RAISE/LOWER TOTAL PRESSURE IF
NECESSARY
      IF ABS(DELTA) > .0005 THEN XH2 = XH2 – DELTA / 5
  6   REM LIQUID PERCENT ADJUSTED
      GOTO 2
 20   REM CONTINUE
      LET PH2O2 = PTOT * YH
      LET PRISE(I, J) = PTOT
      REM ASSUMES PV=NRT WHERE V = 1 LITER
      LET N = PH2O2 / T / R1
      LET WT(I, J) = N * 34 * 1000
      PRINT I, J, WT(I, J), PRISE(I, J)
      NEXT I
NEXT J
END
50 REM YCALC CALCULATES THE WATER VAPOR POLYNOMIAL USING
   REM WATER VAPOR TABLES FROM HANDBOOK OF PHYSICS AND CHEMISTRY
   LET PW=A0+A1*T+A2*T^2+A3*T^3+A4*T^4+A5*T^5+A6*T^6
   LET T = T + 273.16
   REM THE FOLLOWING EQUATIONS ARE TAKEN FROM SCHUMB PAGE 224
   LET UW =(1–XW2)^2*(B0+B1*(1–4*XW2)+B2*(1–2*XW2)*(1–6*XW2))
   LET UH = XW2 ^2 * (B0+B1 * (3–4*XW2)+B2*(1–2*XW2)*(5–6 * XW2))
   LET GAMMAW=EXP((1–XW2)^2/R/T*(B0+B11–4*XW2)B2*(1–2*XW2)*(1–
                                                6*XW2)))
   LET GAMMAH=EXP(XW2^2/R/T*(B0+B1*(3–4*XW2)+B2*(1–2*XW2)*(5–
                                                6*XW2)))
   LET PH=44.576–4025.3/T–12.996*(LOG(T)/LOG(10))+ .0046055 * T
   LET PH = 10 ^ (PH)
   LET PTOT = PW * XW2 * GAMMAW + PH * (1 – XW2) * GAMMAH
   LET YHCALC = PH * XH2 * GAMMAH / PTOT
RETURN
60 REM SUBROUTINE PRINTS THE MOLE FRACTION OF THE H2O2 VAPOR ABOVE
   REM THE H2O2 SOLUTION AS A FUNCTION OF TEMPERATURE
   PRINT "THE MOLE FRACTION OF THE H2O2 VAPOR ABOVE", PERCENT, " %
HYDROGEN PEROXIDE IS"
   PRINT "TEMPERATURE", "FRACTION", "TOTAL PRESSURE"
   FOR I = 0 TO 10 STEP 5
   PRINT I, YH(I), PTOTAL(I)
   NEXT I
RETURN
END
RETURN
END
```

A low-cost chilled mirror hygrometer will preferably be used to determine the percent saturation of the returning air stream. Chilled mirror hygrometers are highly accurate and they hold their calibration for extended periods of time. They are also robust and are less likely to be adversely affected by the oxidative affects of hydrogen peroxide when compared to other humidity sensors. The EdgeTech Model 200 Dew-Trak® Humidity Transmitter is an example of a low cost chilled mirror humidity sensor.

FIG. 5 shows the calculated $H_2O_2$ vapor concentration and the percent saturation for a hydrogen peroxide decontamination cycle performed on a 1000 cubic foot sealed enclosure. The air is continuously humidified to 4.85 mg/liter by the zero degrees centigrade-water bath and sparger system. A four-minute humidification phase is performed with an airflow rate of 200 SCFM. The air flow rate remains at 200 SCFM during the five minute condition phase in which 42 grams per minute of 35% hydrogen peroxide solution is atomized and mixed with the heated, recirculating air stream that has an absolute humidity of 4.85 mg/liter. The $H_2O_2$ vapor concentration at the end of the condition phase is about 1.61 mg/liter and the percent saturation is about 95%. The airflow drops to 32 SCFM and the rate of atomization of 35% hydrogen peroxide drops to 7 grams/min during the decontamination phase. Assuming an $H_2O_2$ vapor half-life of 21.32 minutes, the $H_2O_2$ vapor concentration will drop from 1.61 mg/liter to 1.36 mg/liter over the 45-minute duration of the decontamination phase. The percent saturation will remain in the 90 to 98 percent range during the 45-minute decontamination phase. If the method of the invention were used to provide feedback to control the liquid sterilant atomization rate, the percent saturation could have been maintained between 98 and 99%. The $H_2O_2$ vapor concentration would have still fallen from a high of 1.61 mg/liter to a low of near 1.36 mg/liter. However, the kill potential of the decontamination cycle would have been maximized for the 32 SCFM airflow rate as both the $H_2O_2$ vapor concentration and percent saturation were maximized without the need for a more expensive $H_2O_2$ vapor sensor.

A higher $H_2O_2$ vapor concentration can be obtained by using a higher recirculating airflow rate during the decontamination phase. FIG. 6 shows the calculated $H_2O_2$ vapor concentration and the percent saturation for a hydrogen peroxide decontamination cycle performed on a 1000 cubic foot sealed enclosure. The air is continuously humidified to 4.85 mg/liter by the zero degree centigrade water bath and sparger system. A four-minute humidification phase is performed with an airflow rate of 200 SCFM. The air flow rate remains at 200 SCFM during the five minute condition phase in which 41.2 grams per minute of 35% hydrogen peroxide solution is atomized and mixed with the heated, recirculating are stream that has an absolute humidity of 4.85 mg/liter. The $H_2O_2$ vapor concentration at the end of the condition phase is about 1.56 mg/liter and the percent saturation is about 93%. The airflow drops to 64 SCFM and the rate of atomization of 35% hydrogen peroxide drops to 12.4 grams/min during the decontamination phase. Assuming an $H_2O_2$ vapor half-life of 21.32 minutes, the $H_2O_2$ vapor concentration will only drop from 1.56 mg/liter to 1.50 mg/liter over the 45-minute duration of the decontamination phase. The percent saturation will remain near 99 percent during the 45-minute decontamination phase.

If the enclosure size in FIG. 6 were to increase to 2000 cubic feet with all other parameters unchanged, the decontamination cycle would look more like that in FIG. 7 demonstrating that air exchange rates, rather than air flow rates, will determine the $H_2O_2$ vapor concentration levels and Per Cent Saturation level that can be maintained during a decontamination cycle. The Per Cent Saturation is below 80% in FIG. 7 and the $H_2O_2$ vapor concentration is below 1.2 mg/liter in FIG. 7. In FIG. 6, the Per Cent Saturation was above 90% and the $H_2O_2$ vapor concentration was above 1.5 mg/liter.

The method of the invention provides a system that can be designed to operate over a wide range of airflow rates so that the air exchange rate can be optimized when decontaminating large enclosures. Furthermore, the method of the invention provides feedback that can be used to produce the maximum $H_2O_2$ vapor concentration at a controlled percent saturation for the selected air exchange rate.

As discussed earlier, U.S. Pat. No. 5,876,664, U.S. Pat. No. 5,906,794 and U.S. Pat. No. 5,872,359 all disclose methods of controlling both percent saturation and sterilant vapor concentration. However, they do not go into detail about what action should be taken after the $H_2O_2$ vapor and $H_2O$ vapor concentrations have been measured. A method of controlling $H_2O_2$ concentration and percent saturation based upon an $H_2O_2$ vapor sensor and an $H_2O$ vapor sensor is outlined in steps 1 through 13. The method requires monitoring/knowledge of the $H_2O_2$ vapor concentration, $H_2O$ vapor concentration, airflow rate, enclosure volume, process air temperature, enclosure temperature, current vaporization rate and the half-life HL of the $H_2O_2$ vapor in the enclosure. The method determines the percent saturation and predicts the required change in vaporization rate to achieve saturation within a given length of time. The vaporization rate is then adjusted based upon the prediction. The procedure is repeated throughout the duration of the sterilization cycle.

Vapor Sensor Based Closed Loop Control Method

Step 1: Measure the hydrogen peroxide vapor and water vapor concentrations as well as the temperature of the two vapors
$C_{H2O2}$=3 mg/liter
$C_{H2O}$=7 mg/liter and
T=300° K Step 2: Calculate the weight fraction hydrogen peroxide vapor $$Wt\ \%\ H_2O_2 = \frac{C_{H2O2}}{C_{H2O} + C_{H2O2}} = 0.30$$

Step 3: Calculate the Mole Fraction $H_2O_2$ Vapor, $Y_H$ $$Y_H = \frac{18}{(18+16)/0.30 - 16} =$$

0.1849 = mole fraction liquid($X_H$) since flash vaporized

Step 4: Calculate the mole fraction water vapor, $Y_W$, that equals the mole fraction water, $X_W$, since flash vaporization was used.

$$Y_W = X_W = 1 - Y_H = 1 - 0.1849 = 0.8151$$

Step 5: Calculate the theoretical hydrogen peroxide vapor pressure using equation 21 from Schumb page 225

$$P_{H0} = 10**(\log(P_{H0})\ \text{where}\ \log(P_{H0})\ \text{is defined as follows}$$

$$\log(P_{H0}) = 44.5760 - \frac{4025.3}{T} - 12.996*\log(T) + 0.0046055*T$$

Step 6: Calculate the theoretical water vapor pressure (using the following polynomial that was derived based upon the data in the water vapor tables in the Handbook of Physics and Chemistry).

$$P_{W0} = 4.5767 + 0.33802*T + 0.009989*T^2 +$$
$$0.00024015*T^3 + 0.0000011403*T^4 +$$
$$0.000000030332*T^5 + 0.000000000035945*T^6$$

Step 7: Calculate the total (combined) vapor pressure using equation 22 from page 225 of Schumb $$P = P_{H0}*X_H*\gamma_H + P_{W0}*X_W*\gamma_W = P_{H0}*X_H*\gamma_H + P_{W0}*(1-X_H)*\gamma_W$$

where $\gamma_H$ and $\gamma_W$ are the activity coefficients for hydrogen peroxide and water as defined by equations 23 and 24 on page of Schumb $$\gamma_H = \exp\left[\frac{X_W^2}{R*T}*(B_0 + B_1*(3-4*X_W) + B_2*(1-2*X_W)*(5-6*X_W)\right]\quad \text{EQ 23}$$

$$\gamma_H = \exp\left[\frac{X_H^2}{R*T}*(B_0 + B_1*(1-4*X_W) + B_2*(1-2*X_W)*(1-6*X_W)\right]\quad \text{EQ 24}$$

since $X_H = 1 - X_W$
and where the ideal gas constant R is 1.987
$B_0 = -1017 + 0.97T$, $B_1 = 85$, $B_0 = 13$ Schumb page 225

Step 8: Calculate the theoretical pressure based hydrogen peroxide mole fraction $$Y'_H = \frac{P_{H0}*(1-X_H)*\gamma_H}{P}$$

Step 9: Compare $Y_{H0}$ to $Y'_H$
Step 10(a): If $$Y_{H0}(=0.1849) < \frac{P_{H0}*(1-X_H)*\gamma_H}{P}$$

the $H_2O_2$ vapor is below saturation and the vaporization rate must be increased. Select a new vaporization rate.

Step 10(b): If $$Y_{H0}(=0.1849) < \frac{P_{H0} * (1 - X_H) * \gamma_H}{P}$$

the H$_2$O$_2$ vapor is above saturation and the vaporization rate must be decreased. Select a new vaporization rate.

Step 10(c): If $$Y_{H0}(=0.1849) = \frac{P_{H0} * (1 - X_H) * \gamma_H}{P}$$

the H$_2$O$_2$ vapor is at 100% saturation

Step 11: The future enclosure hydrogen peroxide vapor concentration $C_T$ can be predicted based upon the current concentration $C_o$, the new vaporization concentration $C_{in}$, the enclosure volume V, the circulating air flow rate F, the half life HL of the hydrogen peroxide vapor in the enclosure, and the time interval T.

Step 11(a): Sterilant Degradation is not negligible $$C_T = \left(\frac{F * HL}{F * HL + 0.693 * V}\right) * C_{in} +$$
$$\left(C_o - \left(\frac{F * HL}{F * HL + 0.693 * V}\right) * C_{in}\right) * e^{-(\frac{F}{V} + \frac{0.693}{HL}) * T}$$

Step 11(b): Sterilant degradation is negligible, so HL=∞, and the equation reduces to $$C_T = \left(\frac{1}{1 + (0.693/\infty)/(F/V)}\right) * C_{in} +$$
$$\left(C_o - \left(\frac{1}{1 + (0.693/\infty)/(F/V)}\right) * C_{in}\right) *$$
$$e^{-(\frac{F}{V} + \frac{0.693}{\infty}) * T}$$
$$C_T = C_{in} + (C_o - C_{in}) * e^{-(F/V)T}$$

Step 12: The future enclosure water vapor concentration HT can be predicted based upon the current concentration $H_o$, the new vaporization concentration $C_{in}$, the enclosure volume V, the circulating air flow rate F, the half life of the hydrogen peroxide vapor in the enclosure, the time interval T and the concentration of hydrogen peroxide that is being vaporized.

$$H_T = H_{in} + \left(\frac{V}{F} * \frac{0.693}{HL} * \frac{18}{34}\right) * C_T +$$
$$\left([H_o - H_{in}] - \left(\frac{V}{F} * \frac{0.693}{HL} * \frac{18}{34}\right) * C_o\right) * e^{-(\frac{F}{V} * (T - T_o))}$$

Define $K = \left(\frac{V}{F} * \frac{0693}{HL} + \frac{18}{34}\right)$

Step 13(a): Degradation is not negligible

Then $H_T = H_{in} + K * C_T + ([H_o - H_{in}] - K * C_o) * e^{-(\frac{F}{V} * (T - T_o))}$ Step 13(b): degradation is negligible, so HL=∞, and the equation simplifies as follows Then $K = \left(\frac{V}{F} * \frac{0693}{\infty} * \frac{18}{34}\right) = 0$ Then $H_T = H_{in} + 0 * C_T + ([H_o - H_{in}] - 0 * C_o) * e^{-(\frac{F}{V} * (T_o - T_o))}$ $H_T = H_{in} + (H_o - H_{in}) * e^{-(\frac{F}{V} * (T_o - T_o))}$ Step 14: Recalculate the predicted percent saturation before the adjustment in vaporization rate is made to determine if the adjustment will produce the desired outcome using the method outlined in steps 1 through 9.

Step 14(a): The predicted percent saturation is too high, decrease the new vaporization rate and repeat steps 10 through 12.

Step 14(b): The predicted percent saturation is too low, increase the new vaporization rate and repeat steps 10 through 12.

Step 14(c): The predicted percent saturation is just below 100%, change to the new vaporization rate.

Step 15: Continue to monitor the H$_2$O$_2$ vapor and H$_2$O vapor concentrations and repeat steps 1 through 12 in order to maintain near 100% saturation. The measured change in H$_2$O$_2$ vapor and H$_2$O vapor concentrations will be delayed somewhat based upon the air exchange rate in the enclosure and the response time of the sensors. Adjusting the vaporization rate again before the vapor concentrations have stabilized could push the vapor concentration above the saturation limits and condensation would result.

A simple basic program that is based upon the method disclosed in steps 1 through 15 is contained herein and can be used to control percent saturation. A suitable time delay is required after a change is made in vaporization rate.

```
REM PROGRAM TO ADJUST H2O2 AND H2O VAPOR CONCENTRATIONS TO SATURATION
REM IN TIME DELTAT BASED UPON CURRENT MEASURED CONCENTRATIONS, RETURN
REM AIR TEMP, AIR FLOW RATE, DRY AIR HUMIDITY AND CHAMBER SIZE
DIM YH(100), PTOTAL(100), PRISE(100, 100), WT(100, 100)
COMMON N, RITE2, PRISE, WT
COMMON A0, A1, A2, A3, A4, A5, A6, R, B0, B1, B2, T, L
COMMON C0, C1, C2, C3, C4, C5, C6, D0, D1, D2, D3, D4, D5, D6
COMMON PERCENT, AIRFLOW, INLETCON, ENCLCONC, INJECT, HUMIDITY, TEMP,
VOLUME
COMMON MAXH2O2, DELTAT, DRYAIR
LET A0 = 4.5767
LET A1 = .33802
LET A2 = .009989
```

```
LET A3 = 2.4015E-04
LET A4 = 1.1403E-06
LET A5 = 3.0332E-08
LET A6 = -3.5945E-11
LET D0 = 4.8423
LET D1 = .336
LET D2 = .0099
LET D3 = .0002
LET D4 = .000001
LET D5 = 2E-08
LET D6 = -1E-11
LET L = 0
LET DELTACON = 0
LET R = 1.987
LET R1 = 83.14 / 1.33
REM GAS CONSTANT DEFINED
PRINT "ENTER THE PERCENT H2O2 BY WEIGHT ="
INPUT PERCENT
PERCENT = PERCENT / 100
PRINT "ENTER THE ENCLOSURE VOLUME IN CUBIC FEET"
INPUT VOLUME
LET VOLUME = 28.32 * VOLUME
PRINT "ENTER THE AIRFLOW RATE IN SCFM"
INPUT AIRFLOW
LET AIRFLOW = 28.32 * AIRFLOW
PRINT "ENTER THE COME-UP RESPONSE TIME"
INPUT DELTAT
PRINT "ENTER THE RETURNING VAPOR TEMPERATURE IN DEGREES C"
INPUT TEMP
PRINT "ENTER THE HUMIDITY OF THE DRY AIR IN MG/LITER"
INPUT DRYAIR
PRINT "ENTER THE ENCLOSURE H2O2 CONC IN MG/LITER"
INPUT ENCLCONC
LET ENCLCONCo = ENCLCONC
LET INLETCON = ENCLCONC
LET INLETCONo = INLETCON
PRINT "ENTER THE ENCLOSURE HUMIDITY IN MG/LITER"
INPUT HUMIDITY
LET HUMIDITYo = HUMIDITY
    PRINT "INLET CONC", "ENCL CONC", "MAXH2O2", "ITERATIONS"
3   REM CONTROL LOOP
LET XH = (18.01 / (34 / PERCENT - 15.994))
LET XW = 1 - XH
LET XW2 = XW
LET XH2 = XH
REM CALCULATE USING RETURN VAPOR TEMPERATURE
LET T = TEMP
LET B0 = -752 + .97 * T
LET B1 = 85
LET B2 = 13
GOSUB 50
LET YH(I) = YHCALC
LET PTOTAL(I) = PTOT
1   REM CONTINUE
REM ASSUME FLASH VAPORIZATION IS UTILIZED
REM USE POLYNOMIAL AT 50C FOR 1ST ESTIMATE
REM CALCULATE MAXIMUM H2O2 THAT CAN BE FLASHED
LET C0 = .14495
LET C1 = 4.1606
LET C2 = -9.3985
LET C3 = 7.2227
LET C4 = 0
LET C5 = 0
LET C6 = 0
REM CALCULATE SATURATION CONCENTRATIONS FOR H2O2 AND H20 AT TEMP
    REM CALCULATE THE WATER VAPOR CONCENTRATION POLYNOMIAL USING
    REM WATER VAPOR TABLES FROM HANDBOOK OF PHYSICS AND CHEMISTRY
        LET SATURATE = 0+D1*TEMP+D2*TEMP^2+D3*TEMP^3+D4*TEMP^4+
                                   D5*TEMP^5+D6*TEMP^6
        LET RH = HUMIDITY / SATURATE
    REM ITERATE TO FIND H2O2 VAPOR CONCENTRATION
        REM XH2 IS THE FIRST ESTIMATE OF THE LIQUID PERCENTAGE
        LET XH2 = C0+C1*XH+C2*XH^2+C3*XH^3+C4*XH^4+C5*XH^5+C6*XH^6
2       REM CONTINUE
        LET XW2 = 1 - XH2
        T = TEMP
        GOSUB 50
        LET PW = PW * RH
5       LET YH = (PTOT - PW) * XH / PTOT
        LET DELTA = YHCALC - YH
```

```
        IF ABS(DELTA) <= .001 THEN 20
        REM REDUCE LIQUID PERCENT TO RAISE TOTAL PRESSURE IF NECESSARY
        IF DELTA > .001 THEN XH2 = XH2 – DELTA / 5
        GOTO 6
        REM INCREASE LIQUID PERCENT TO LOWER TOTAL PRESSURE IF NECESSARY
        IF DELTA < –.001 THEN XH2 = XH2 + DELTA / 10
6       REM LIQUID PERCENT ADJUSTED
        GOTO 2
20      REM CONTINUE
        LET PH2O2 = PTOT * YH
        LET PRISE(I, J) = PTOT
        REM ASSUMES PV=NRT WHERE V = 1 LITER
        LET N = PH2O2 / T / R1
        LET MAXH2O2 = N * 34 * 1000
        REM SATURATION CONDITIONS ARE NOW KNOWN
REM MUST ADJUST TO REACH SATURATION
        PRINT INLETCON, ENCLCONC, MAXH2O2, L
        PERCENTSAT = ENCLCONC / MAXH2O2 * 100
30      REM ASSUME DEGRADATION IS NEGLIGIBLE FOR INJECTION CALCULATION
        REM CALCULATE THE NEW INLET CONCENTRATION
        LET DELTACON = DELTACON + (MAXH2O2 – ENCLCONC)
        IF ABS(ENCLCONC – MAXH2O2) < .01 THEN 40
        LET AIREXCH = AIRFLOW / VOLUME
        LET INLETCON = INLETCONo + .75 * DELTACON
        LET ENCLCONC=INLETCON+(ENCLCONCo–INLETCON)* EXP(–AIREXCH * DELTAT)
        LET H2OFRAC = (1 – PERCENT) / PERCENT
        LET HUMIDITY=H2OFRAC*INLETCON+DRYAIR+(HUMIDITYo–H2OFRAC*INLETCON
                              – DRYAIR)*EXP(–AIREXCH*DELTAT)
        LET L = L + 1
        GOTO 3
40      REM CONTINUE
        PRINT "TEMPERATURE", "MAXH2O2", "H2O2 SAT", "HUMIDITY"
        PRINT "IN DEGREES C", "IN MG/LITER", "IN PERCENT", "FRACTION OF 1"
        PRINT TEMP, MAXH2O2, PERCENTSAT, RH
        PRINT "INLET CONC", "ENCL CONC", "HUMIDITY", "ITERATIONS"
        PRINT INLETCON, ENCLCONC, HUMIDITY, L
END
50 REM YCALC CALCULATES THE WATER VAPOR PRESSURE POLYNOMIAL USING
   REM WATER VAPOR TABLES FROM HANDBOOK OF PHYSICS AND CHEMISTRY
        LET PW = A0+A1*T+A2*T^2+A3*T^3+A4*T^4+A5*T^5+A6*T^6
        LET T = T + 273.16
        REM THE FOLLOWING EQUATIONS ARE TAKEN FROM SCHUMB STARTING ON PAGE
224
        LET UW = (1–XW2)^2*(B0+B1*(1–4*XW2)+B2*(1–2*XW2)*(1–6*XW2))
        LET UH = XW2^2*(B0+B1*(3–4*XW2)+B2*(1–2*XW2)*(5–6*XW2))
        LET GAMMAW=EXP((1–XW2)^2/R/T*(B0+B1*(1–4*XW2)+B2*(1–2*XW2)*(1–
                                                                  6*XW2)))
        LET GAMMAH = EXP(XW2^2/R/T*(B0+B1*(3–4*XW2)+B21–2*XW2)*(5–6*XW2)))
        LET PH = 44.576 – 4025.3 / T – 12.996* LOG(T) / LOG(10)+.0046055 * T
        LET PH = 10 ^ (PH)
        LET PTOT = PW * XW2 * GAMMAW + PH * (1 – XW2) * GAMMAH
        LET YHCALC = PH * XH2 * GAMMAH / PTOT
RETURN
END
```

The monitoring and control based upon the feedback from the $H_2O_2$ vapor sensor and $H_2O$ vapor sensor can avoid condensation if the sensors response to the change in injection rate is in a timely manner and if a second change in vaporization rate is not made too quickly. However, waiting too long to change the vaporization rate may result in a less than optimum decontamination cycle.

A control system based upon feedback from a dew point sensor will face a similar response issue. Ideally, a dewpoint sensor based system will increase the vaporization rate until the dewpoint is only a degree or so below the measured temperature of the carrier air stream containing the sterilant vapor and the water vapor.

The sterilant vapor concentration, $C_t$, in a flowing mixer (with no degradation) as a function of time based upon the initial concentration, $C_o$, based upon the inlet concentration, $C_{in}$, the air flow rate, $F$, and the enclosure volume, $V$, is defined by equation 4 assuming nearly instantaneous uniform mixing of the sterilant vapor throughout the sealable enclosure.

$$Ct = C_{in} + (C_o - C_{in}) * e^{-(F/V*T)} \qquad \text{Equation 4}$$

Table 6 contains hydrogen peroxide vapor concentration values for the first minute after an enclosure initially at a hydrogen peroxide vapor concentration of 1 mg/liter is exposed to various airflows containing 2 mg/liter of hydrogen peroxide vapor. The airflows are expressed as a fraction of sealable enclosure volume.

It is obvious based upon the data contained in Table 6 that closed loop feedback from a vapor sensor or a dew point sensor will be delayed significantly even for air exchange rates that are capable of changing the volume of the sealable enclosure once every minute.

TABLE 6

Enclosure Concentration when 2 mg/l is introduced into an enclosure initially at 1 mg/l

| Time (min) | Carrier gas flow rate divided by sealable enclosure volume (air exchanges per minute) | | | | | | | | | |
|---|---|---|---|---|---|---|---|---|---|---|
| | 0.1 | 0.2 | 0.3 | 0.4 | 0.5 | 0.6 | 0.7 | 0.8 | 0.9 | 1 |
| 0.1 | 1.01 | 1.02 | 1.03 | 1.04 | 1.05 | 1.06 | 1.07 | 1.08 | 1.09 | 1.10 |
| 0.2 | 1.02 | 1.04 | 1.06 | 1.08 | 1.10 | 1.11 | 1.13 | 1.15 | 1.16 | 1.18 |
| 0.3 | 1.03 | 1.06 | 1.09 | 1.11 | 1.14 | 1.16 | 1.19 | 1.21 | 1.24 | 1.26 |
| 0.4 | 1.04 | 1.08 | 1.11 | 1.15 | 1.18 | 1.21 | 1.24 | 1.27 | 1.30 | 1.33 |
| 0.5 | 1.05 | 1.10 | 1.14 | 1.18 | 1.22 | 1.26 | 1.30 | 1.33 | 1.36 | 1.39 |
| 0.6 | 1.06 | 1.11 | 1.16 | 1.21 | 1.26 | 1.30 | 1.34 | 1.38 | 1.42 | 1.45 |
| 0.7 | 1.07 | 1.13 | 1.19 | 1.24 | 1.30 | 1.34 | 1.39 | 1.43 | 1.47 | 1.50 |
| 0.8 | 1.08 | 1.15 | 1.21 | 1.27 | 1.33 | 1.38 | 1.43 | 1.47 | 1.51 | 1.55 |
| 0.9 | 1.09 | 1.16 | 1.24 | 1.30 | 1.36 | 1.42 | 1.47 | 1.51 | 1.56 | 1.59 |
| 1 | 1.10 | 1.18 | 1.26 | 1.33 | 1.39 | 1.45 | 1.50 | 1.55 | 1.59 | 1.63 |

The method of the invention provides an opportunity for the decontamination system to "learn" and "remember" the response of a system to changes in vaporization rate. An automated routine is performed by the decontamination system starting at below saturation conditions. For example, the system may incrementally increase the vaporization rate in steps of 5% when it is running at 75%, 85% and 95% saturation so that it can measure and record the response of the system. Alternately, the learned behavior can be expanded to include changes in airflow rates (with corresponding increases in vaporization rate) in addition to changes in just the vaporization rate. For example, the air exchange rate can be increased in increments of 5% when it is running at 75%, 85% and 95% saturation. The vaporization concentration will be held constant by increasing the vaporization rate by 5% each time the air exchange rate is increased 5%.

This learned behavior could be stored in non-volatile memory for use when running decontamination cycles on the particular enclosure. Learned behavior data can be stored for multiple enclosures. The software can later refer to this learned behavior data when adjusting the vaporization rate and/or air flow in conjunction with the vaporization rate.

The "learned" and "remembered" behavior method can be applied to a closed loop control system that is using a dew point sensor or to a closed loop control system that controls based upon the readings of an $H_2O_2$ vapor sensor and an $H_2O$ vapor sensor.

BRIEF DESCRIPTION OF THE FIGURES

FIG. 1 is a Phase Diagram for Calcium Chloride and Water Solutions.

FIG. 2 is a graph of the outlet flow for a peristaltic pump over a wide range of pump inlet pressures.

FIG. 3 is a graph of the ratio of the actual outlet flow to the nominal outlet flow (zero inlet pressure) over a wide range of pump inlet pressures and pump speeds (flow rates) for a peristaltic pump.

FIG. 4 is graph of the actual outlet flow rate for a peristaltic pump over a wide range of pump outlet pressures.

FIG. 5 is a graph of hydrogen peroxide vapor concentration, water vapor concentration and percent saturation during all but the aeration phase of a decontamination cycle with 32 SCFM air flow during the sterilization phase of a 1000 cubic foot sealed enclosure.

FIG. 6 is a graph of hydrogen peroxide vapor concentration, water vapor concentration and percent saturation during all but the aeration phase of a decontamination cycle with 64 SCFM air flow during the sterilization phase of a 1000 cubic foot sealed enclosure.

FIG. 7 is a graph of hydrogen peroxide vapor concentration, water vapor concentration and percent saturation during all but the aeration phase of a decontamination cycle with 64 SCFM air flow during the sterilization phase of a 2000 cubic foot sealed enclosure.

FIG. 8 is a schematic of an entire system that is capable of practicing the art of the present invention.

FIG. 9 is a schematic of a lower cost system that is capable of practicing the art of the present invention.

FIG. 10 is a Closed Loop Humidification System Test Set-up per the present invention.

FIG. 11 is an Open Loop Humidification System Test Set-up per the present invention.

FIG. 12 is an embodiment of a liquid sterilant delivery system with feedback control as disclosed in the art of the present invention.

FIG. 13 is another embodiment of a liquid sterilant delivery system with feedback control as disclosed in the art of the present invention.

FIG. 14 is an exploded view of a low compression ratio water ring pump as described in the art of the present invention.

FIG. 15 is a section view of a low compression ratio water ring pump as described in the art of the present invention.

FIG. 16 is a sketch of a Dual Modified Tesla Turbine Air Pump with Excess Moisture Separator FIG. 17 is the schematic of FIG. 8 with an excess moisture coalescing element and with the dewpoint sensor relocated.

FIGS. 18(a) and 18(b) are side and bottom views of an embodiment of a cold-water bath per the present invention.

FIG. 19 is a schematic of an embodiment of the present invention with the blower downstream of the cold water bath disclosed in FIG. 18.

FIG. 20 is a graph of the learned response of the enclosure of example 1 to an inlet water vapor concentration of 30 mg/liter with 0.1 enclosure air exchanges per minute.

FIG. 21 is a graph of the learned response of the enclosure of example 2 to an inlet 35% $H_2O_2$-65% $H_2O$ vaporization rate of 30 grams per minute with a 50 SCFM air flow into the 1000 foot enclosure.

FIG. 22 is a graph of a decontamination cycle that uses the learned response from example 2 to bring the system up to near saturation and then attempts to maintain it with a vaporization rate of 10 grams per minute.

FIG. 23 is a graph of a decontamination cycle that uses the learned response from example 2 to bring the system up to near saturation and then attempts to maintain it with a vaporization rate of 12 grams per minute.

FIG. 24 is a graph of a decontamination cycle that uses the learned response from example 2 to bring the system up to near saturation and then attempts to maintain it with a vaporization rate of 13 grams per minute.

DETAILED DESCRIPTION OF THE INVENTION

The method of the invention can be used to optimize the efficacy of vapor phase decontamination in either closed, or open loop, flow through cycles. The term "decontamination: will be understood to include sterilization, dis-infection and sanitization.

The sterilant vapor preferably is generated by flash vaporizing 30 to 35% by weight hydrogen peroxide solution to produce hydrogen peroxide vapor and water vapor; however, it could be generated by vaporizing other combinations of liquids such as peracetic acid, hydrogen peroxide and water. The carrier gas preferably is air; however, other carrier gases such as nitrogen can also be used. For the purposes of describing some of the embodiments, the carrier gas will be air and the sterilant vapor will be vapor phase hydrogen peroxide generated by flash vaporizing an aqueous solution of hydrogen peroxide.

In the method, a flow of carrier gas is circulated in a closed loop circuit that leads into, through and out of a sealable enclosure. The aqueous solution of hydrogen peroxide is atomized and delivered into the warm carrier gas flow where it vaporizes on its way to the sealable enclosure. As the vapor flows through the enclosure, it contacts all of the surfaces in the enclosure as well as the surfaces of its contents and decontaminates them. After the carrier gas exits the sealable enclosure, it passes through a cold-water bath that removes the sterilant vapors and humidifies the air stream. The carrier gas is warmed and returned to the sealable enclosure again laden with sterilant vapors. This circulation of the carrier gas continues for a pre-determined time that is known to affect decontamination of the sealable enclosure and its contents.

The method succeeds in optimizing decontamination by using a chilled mirror humidity sensor to bring the combined hydrogen peroxide and water vapor concentration up to near saturation conditions. The method "learns" the response of the sealable enclosure to changes in the vaporization rate and uses the "remembered" response data to optimally adjust the vaporization rate to maintain near saturation conditions within the enclosure.

In the method of the present invention, the sterilant vapor concentration is monitored by measuring the vaporization rate; however, it is not the primary control in the feedback loop. The dew point of hydrogen peroxide vapor and water vapor laden carrier air stream is the primary control in the feedback loop. This dew point is maintained as close as practically possible to the actual carrier gas temperature so that near saturation conditions are present within the sealable enclosure. This method of control automatically maximizes the sterilant vapor concentration within the sealed enclosure resulting in maximized kill potentials and an efficient decontamination.

The simplicity of the present invention can be appreciated by inspecting FIGS. 8 and 9. The method of the invention will now be described with reference to FIG. 8. As shown, the recirculating flow-through decontamination system of the invention includes a sealable enclosure 1, an inlet port 7 and an outlet port 3. HEPA (or ULPA) filters, 2 and 9, are preferably placed in line between the enclosure 1 and the inlet and outlet ports 3 and 7 to preventingress (or leakage) of bioburden from enclosure 1, A dew point sensor 5, preferably a chilled mirror hygrometer, is located in the conduit 4 that is connected to the enclosure outlet 3. Conduit 4 is connected to the inlet of the decontamination system 10 that in turn is connected to the air blower 20 which may be of any known type. The outflow from air blower 20 flows into sparger 30 that is submerged in cold-water bath 40. The air stream is broken into tiny bubbles by the sparger so that the air stream and the vapor it contains equilibrates with the temperature of cold water bath 40. Water and sterilant vapor that are in excess of the dew point concentrations based upon the water temperature condense into the water 120 in water bath 40. If the air stream is dry, water vapor is picked up by the air stream until it is in dew point equilibrium with water bath 40. The humidified air stream exits cold-water bath 40 and passes through conduit 50 and into heat exchanger 60 that warms the air. The warmed air enters conduit 70, which contains process air heater 75, and temperature sensor T1. Heater 75 elevates the temperature of the carrier air stream to the desired temperature as measured by temperature sensor T1. The desired temperature will be equal to the enclosure ambient temperature except when atomized sterilant is being introduced into the air stream. The temperature of the carrier air stream will be elevated whenever atomized sterilant needs to be vaporized. Atomizer 80, which is preferably an ultrasonic nozzle, delivers atomized liquid sterilant into the heated carrier air stream when a decontamination cycle is in the condition or sterilize phases. Temperature sensor T2 monitors the temperature of the vaporization process within the carrier air stream and can be used to provide closed loop feedback to control the temperature of air process heater 75. Carrier air flow sensor 90 monitors the airflow rate in conduit 100 as the sterilant laden air stream is returned to enclosure 1 through conduit 7 and filter 9. The sterilant-laden air passes through enclosure 1, through filter 2 and outlet port 3, down conduit 4 and past dew point sensor 5 as it is drawn through air pump inlet 10 and into air pump 20.

Valve 12, inlet conduit 14, and filter 16 are also connected to the inlet (suction side) of air blower 20. When valve 12 is opened, filtered air is drawn into the system from a source other than the sealed enclosure. This allows the system pressure to be increased. Filter 16 is also a HEPA or an ULPA filter. Valve 72, outlet conduit 74 and filter 76 are also connected to conduit 70. When valve 72 is opened, filtered air is discharged from the system to a destination other than the sealed enclosure. This allows the system pressure to be decreased. Filter 76 is also a HEPA or an ULPA filter. Appropriate pressure transducers (not shown) can be placed within the decontamination system as well as within enclosure 1 for pressure monitoring and control purposes.

Cold-water bath 40 can be chilled using a refrigeration system. Compressor 140 draws refrigerant through header 122 and conduit 130 from the evaporator coils 110 that pass through the cold-water bath and contact the water 120. The refrigerant is compressed and passed through the top half of condensers 160 and 170, header 176 and the bottom half of condensers 160 and 170 before it is allowed to expand as if passes across orifice 180 and expands into conduit 190, header 126 and top evaporator coils 110, header 124 and bottom evaporator coils 110. Temperature sensor T3 is used to provide feedback to the refrigeration system. Condenser 160 can act as heat exchanger 60 for the carrier air stream. The external heat exchange medium for condenser 170 can be air or water.

The delivery system that supplies the liquid sterilant to the atomization nozzle 80 can be of any known type including those disclosed in FIG. 9 and FIG. 10.

Heat exchanger 200 allows liquid to be discharged from cold-water bath 40 and to be replaced with fresh water. Liquid flows out of water bath 40 when valve 206 is opened and through conduit 208 into heat exchanger 200, out conduit 204 and into drain 210. Fresh water flows into the other side of heat exchanger 200 through conduit 202, out conduit 203 through valve 205 and into cold-water bath 40. The fresh water enters the cold-water bath at a temperature nearly equal to the water exiting cold-water bath 40 because the cold water passing through heat exchanger 200 cools it. The water used in the systems illustrated by FIG. 8, 9, 17 or 19 should, at a minimum, be demineralized so that mineral deposits do not build up in the system and adversely affect its operation.

The system shown in FIG. 9 is the same as FIG. 8 except the refrigeration system has been eliminated. Ice is used to chill the cold-water bath. Enough ice can be placed in the system at the start of the decontamination process to complete the run, or ice can be added during the run. The ice can be added by any known means. Temperature sensor T3 will alert the operator if the temperature of water bath 40 starts to rise and more ice is needed.

Salt can be added to the cold-water bath to lower the temperature of the water bath to below 32° F. (0° C.). Closed loop humidification test setup 700, refer to FIG. 10, and open loop humidification test setup 701, refer to FIG. 11, were constructed using 2-34.5-ounce plastic Folgers coffee cans 710, a twenty foot coil of ¼ inch ID soft copper tubing 720, two SMC Pneumatics #10-32 sintered bronze exhaust mufflers 730 some clear PVC tubing 740, a small diaphragm air pump 750, some ice 760, some Morton Rock Salt for Ice Cream making 770, two humidity/temperature probes 780, 785 and a submersible temperature probe 790.

Table 6 contains the data obtained from closed loop test setup 700. The relative humidity of the recirculating air fell to about 50% at a temperature that was below the normal freezing point of water.

TABLE 6

Humidty of Air Stream Recirculating through a Closed Loop Through Cold Water Bath

| Sensor 780 | | | Sensor 785 | | | Sensor 790 |
|---|---|---|---|---|---|---|
| Time (HH:MM) | Temp (deg F.) | RH (%) | Time (HH:MM) | Temp (deg F.) | RH (%) | Temp (deg F.) |
| 11:08 | 71.2 | 58% | 11:07 | 70.5 | 56% | 23.2 |
| 11:10 | 55.2 | 59% | 11:09 | 55.6 | 56% | 14 |
| 11:12 | 46.2 | 59% | 11:11 | 46.9 | 56% | 11.3 |
| 11:14 | 41.9 | 58% | 11:13 | 42.6 | 56% | 9.9 |
| 11:16 | 37.6 | 58% | 11:15 | 38.5 | 55% | 8.1 |
| 11:18 | 35.4 | 58% | 11:17 | 36.1 | 55% | 7.2 |
| 11:20 | 33.1 | 58% | 11:19 | 34 | 55% | 6.1 |
| 11:22 | 31.8 | 57% | 11:21 | 32.7 | 55% | 5.4 |
| 11:24 | 30.4 | 57% | 11:23 | 31.6 | 55% | 4.6 |
| 11:26 | 29.5 | 57% | 11:25 | 30.7 | 55% | 4.1 |
| 11:28 | 29.1 | 57% | 11:27 | 30 | 55% | 3.6 |
| 11:30 | 28.4 | 57% | 11:29 | 29.5 | 55% | 3 |
| 11:32 | 28.2 | 57% | 11:31 | 29.1 | 55% | 2.7 |
| 11:34 | 28.2 | 57% | 11:33 | 28.6 | 55% | 2.3 |
| 11:36 | 27.7 | 57% | 11:35 | 28.4 | 55% | 2.1 |
| 11:38 | 27.5 | 57% | 11:37 | 28.2 | 55% | 1.8 |
| 11:40 | 27.3 | 58% | 11:39 | 28.2 | 56% | 1.6 |
| 11:42 | 27.3 | 57% | 11:41 | 28.2 | 55% | 1.4 |
| 11:44 | 27.3 | 57% | 11:43 | 28.2 | 55% | 1.4 |
| 11:46 | 27.1 | 57% | 11:45 | 28.2 | 55% | 1.4 |
| 11:48 | 27.1 | 57% | 11:47 | 28.2 | 55% | 0.9 |
| 11:50 | 27.1 | 57% | 11:49 | 28.2 | 55% | 0.9 |
| 11:52 | 27.1 | 57% | 11:51 | 28.2 | 55% | 0.5 |
| 11:54 | 27.3 | 56% | 11:53 | 28.2 | 54% | 0.5 |
| 11:56 | 27.3 | 56% | 11:55 | 28.2 | 55% | 0.5 |
| 11:58 | 27.3 | 53% | 11:57 | 28.2 | 52% | 0.3 |
| 12:00 | 27.3 | 52% | 11:59 | 28.2 | 51% | 0.3 |
| 12:02 | 27.5 | 52% | 12:01 | 28.2 | 51% | 0.3 |
| 12:04 | 27.7 | 51% | 12:03 | 28.2 | 50% | 0.3 |
| 12:06 | 28.2 | 51% | 12:05 | 28.6 | 49% | 0.1 |
| 12:08 | 28.2 | 50% | 12:07 | 28.9 | 49% | 0.1 |

Table 7 contains the data obtained using open loop setup 701. The absolute humidity of the outlet of the flowing air stream quickly equilibrated at just below 2.2 mg/liter with an inlet absolute humidity of a little over 11 mg/liter. The water bath temperature was well below the normal freezing point of water.

TABLE 7

Humidity of Single Pass Air Stream Through Cold Water Bath

| Inlet Sensor 785 | | | | Outlet Sensor 780 | | | | Sensor 790 | Calculated Absolute Humidity | |
|---|---|---|---|---|---|---|---|---|---|---|
| Time (H:M) | Temp (deg F.) | Temp (deg C.) | RH (%) | Time (H:M) | Temp (deg F.) | Temp (deg C.) | RH (%) | Temp (deg F.) | Inlet AH (mg/l) | Outlet AH (mg/l) |
| 12:23 | 76.9 | 24.9 | 49% | 12:22 | 32.9 | 0.5 | 46% | 0.3 | 11.46 | 2.31 |
| 12:24 | 76.8 | 24.9 | 49% | 12:23 | 32.7 | 0.4 | 46% | 0.3 | 11.43 | 2.29 |
| 12:25 | 77 | 25.0 | 50% | 12:24 | 32.5 | 0.3 | 47% | 0.1 | 11.73 | 2.32 |
| 12:26 | 76.8 | 24.9 | 49% | 12:25 | 32.2 | 0.1 | 45% | 0.1 | 11.43 | 2.20 |
| 12:27 | 77 | 25.0 | 48% | 12:26 | 32.2 | 0.1 | 45% | 0.1 | 11.26 | 2.20 |
| 12:28 | 76.8 | 24.9 | 48% | 12:27 | 32 | 0.0 | 45% | 0.1 | 11.19 | 2.18 |
| 12:29 | 76.8 | 24.9 | 47% | 12:28 | 32 | 0.0 | 45% | 0.1 | 10.96 | 2.18 |
| 12:30 | 76.8 | 24.9 | 47% | 12:29 | 31.8 | −0.1 | 45% | 0.1 | 10.96 | 2.16 |
| 12:31 | 76.8 | 24.9 | 48% | 12:30 | 31.8 | −0.1 | 45% | 0.1 | 11.19 | 2.16 |
| 12:32 | 76.8 | 24.9 | 47% | 12:31 | 31.8 | −0.1 | 45% | 0.1 | 10.96 | 2.16 |
| 12:33 | 76.8 | 24.9 | 48% | 12:32 | 31.8 | −0.1 | 46% | −0.2 | 11.19 | 2.21 |
| 12:34 | 76.8 | 24.9 | 49% | 12:33 | 31.8 | −0.1 | 46% | −0.2 | 11.43 | 2.21 |
| 12:35 | 77 | 25.0 | 49% | 12:34 | 31.8 | −0.1 | 46% | −0.2 | 11.50 | 2.21 |
| 12:36 | 76.8 | 24.9 | 48% | 12:35 | 31.8 | −0.1 | 46% | −0.2 | 11.19 | 2.21 |
| 12:37 | 76.8 | 24.9 | 48% | 12:36 | 31.8 | −0.1 | 45% | −0.2 | 11.19 | 2.16 |
| 12:38 | 76.8 | 24.9 | 48% | 12:37 | 31.8 | −0.1 | 45% | −0.2 | 11.19 | 2.16 |
| 12:39 | 77 | 25.0 | 48% | 12:38 | 31.8 | −0.1 | 45% | −0.2 | 11.26 | 2.16 |
| 12:40 | 77.2 | 25.1 | 48% | 12:39 | 31.8 | −0.1 | 45% | −0.2 | 11.34 | 2.16 |
| 12:41 | 77.5 | 25.3 | 48% | 12:40 | 31.8 | −0.1 | 45% | −0.2 | 11.45 | 2.16 |

TABLE 7-continued

Humidity of Single Pass Air Stream Through Cold Water Bath

| Inlet Sensor 785 | | | | Outlet Sensor 780 | | | | Sensor 790 | Calculated Absolute Humidity | |
|---|---|---|---|---|---|---|---|---|---|---|
| Time (H:M) | Temp (deg F.) | Temp (deg C.) | RH (%) | Time (H:M) | Temp (deg F.) | Temp (deg C.) | RH (%) | Temp (deg F.) | Inlet AH (mg/l) | Outlet AH (mg/l) |
| 12:42 | 77.2 | 25.1 | 47% | 12:41 | 31.8 | −0.1 | 45% | −0.2 | 11.10 | 2.16 |
| 12:43 | 77.2 | 25.1 | 48% | 12:42 | 31.8 | −0.1 | 45% | −0.2 | 11.34 | 2.16 |

The outlet humidity of the air passing through the water and "ice cream salt" mixture is below that attainable with a continuous duty desiccant wheel system and is approaching that attainable with a batch desiccant system. The outlet humidity and temperature can be maintained indefinitely as long as ice is present whereas the outlet humidity and temperature will both rise over time with a batch desiccant system.

FIGS. 18(*a*) and 18(*b*) disclose a cold water bath 800 filled with a water based solution 810. Spargers 820 and 830 break incoming air streams 840 and 850 into tiny air bubbles 860 that are propelled by their low density to the surface of water based solution 810. Sloped baffles 870, 872, 874 and 876 force air bubbles to travel a long distance through the cold-water solution on their way to the surface. The air bubbles are cooled to nearly the same temperature as the cold-water solution before they reach the surface. Any excess moisture that is present in the form of super-cooled water vapor in air bubbles 860 condenses on the surface of sloped baffles 870, 872, 874 or 876 so that the humidity of the air stream exiting the cold-water bath is reduced to the saturation concentration of the cold-water bath. If the moisture content of air bubbles 860 is less than saturation at the temperature of cold-water 810 in bath 800, air bubbles 860 pick up moisture until they are saturated at the temperature of cold-water 810 in bath 800. The humidity of air stream 880 exiting cold-water bath 800 is thus determined by the temperature of cold water 810 in bath 800. Refrigeration coils 890 are used to maintain the temperature of cold-water 810 in bath 800. A solute such as Calcium Chloride or Lithium Chloride can be added to cold-water 810 in bath 800 to lower the temperature to below 32° F. (0° C.).

The system shown in FIG. 17 is essentially the same as the system shown in FIG. 8 except that dew point sensor 5 has been relocated to be contained within sealed enclosure 1 instead of within conduit 4 and coalescing filter 450 has been added so that the carrier air stream exiting cold water bath 40 will have to pass through said coalescing filter. Any moisture than is in said air stream that is in excess of saturation will accumulate on coalescing filter 450 and fall back into cold-water bath 40 before said airstream enters conduit 70.

Refer to FIG. 16 wherein modified Tesla turbine 400 is used both as an air pump and as an excess water vapor removal system. The carrier air exiting cold-water bath 40 in any of FIG. 8, 9, 17 or 19 is drawn into inlet 402 of turbine 400 by suction created by spinning disks 404. Motor 408 spins disks 404 at a high rotational speed. The friction between the air and the spinning disks pulls the air between disks 404 in a spiral flow path that works its way out towards the tips of disks 404 where the air flow exits the disks nearly tangential to the disks at a velocity nearly equal to that of the tips of disks 404. The air stream, and any excess moisture that gathers on the outer walls of flow conduit 406, travel towards turbine outlet port 410. The speed of the carrier airflow slows down as it enters expansion chamber 420 and the air speed is converted into pressure. Excess moisture adheres to sloped airflow guide 430 and passes through the perforations in guide 430 and accumulates in reservoir 440. The carrier air continues on through coalescing filter 450 and into heater exchanger 60 (or heater exchanger 160) in any of FIG. 8, 9, 17 or 19. Any remaining excess moisture in the carrier air stream will accumulate on coalescing filter 450 and fall back down onto perforated airflow guide 430 and into reservoir 440.

Liquid droplets will not damage modified Tesla turbine 400 as it would other types of blowers because all of the surfaces are smooth and use friction to move combinations of gases, liquids or powders without fear of damage to the turbine disks.

The other half of the dual Tesla turbine can be used as air pump 20 in any of FIG. 8, 9, 17 or 19 that draws air from enclosure 1 through outlet port 3, through conduit 4 and into the decontamination system.

Carrier airflow sensor 90 is shown located in outlet conduit 100 in the systems shown in FIGS. 8, 9, 17 and 19 but could be located elsewhere. Airflow sensor 90 can be any of a number of types of air flow sensors. A pitot tube flow sensor is an example of a low cost flow sensor that operates over a wide flow range and holds its calibration well over time. Turbine anemometers and mass flow meters could also be used for airflow sensor 90. It may be necessary to install a pressure sensor near airflow sensor 90 and to attach a pressure sensor to enclosure 1. This will allow for corrections to be made for differences in the pressure within enclosure 1 from one time to another as well as for flow restrictions in conduit 7 and filter 9 that may differ from one time to another.

The operation of the dew point control "learn" and "remember" process can be understood by working through a simplified example. Simplified example 1 will use water vapor only.

Example 1

Dew Point Control Algorithm

An enclosure is at an initial humidity, Ct, of 11.5 mg/liter. The chilled mirror sensors indicate that the dew point, or temperature at which 11.5 mg/liter would be 100% saturated, is about 13.2° C. An airflow that changes the volume in the enclosure once every 10 minutes carries 30 mg/liter of water vapor into the enclosure and exits with a water vapor concentration Ct. The dew point sensor measures the dew point temperature and records it in column two of Table 8 once every minute. The temperature of the air and water vapor within the enclosure is 25° C. The actual water vapor concentration within the enclosure is calculated for this temperature by interpolating between the appropriate dew point temperature values from columns 1, 3, 5 or 7 of Table 9 and entered in column three of Table 8. The PerCent saturation is calculated by dividing the value for Ct in column 3 of Table 8 by 23.04 mg/l (saturation at 25° C.).

TABLE 8

Dew Point Control "Learn" and "Remember"

| Elapsed Time (min) | Dew Point Temperature (deg C.) | Ct mg/l | Percent Saturation |
|---|---|---|---|
| 0 | 13.2 | 11.52 | 50% |
| 1 | 15.56 | 13.27 | 57.6% |
| 2 | 17.22 | 14.67 | 63.7% |
| 3 | 18.89 | 16.20 | 70.3% |
| 4 | 20 | 17.29 | 75% |
| 5 | 21.11 | 18.45 | 80% |
| 6 | 22.22 | 19.67 | 85.4% |
| 7 | 23.33 | 20.96 | 91% |
| 8 | 23.89 | 21.64 | 93.9% |
| 9 | 24.44 | 22.33 | 96.9% |
| 10 | 24.8 | 22.88 | 99.3% |

TABLE 9

Water Vapor Concentration at Various Dew Point Temperatures

| Dew Point (degrees C.) | H$_2$0 SAT mg/l | Dew Point (degrees C.) | H20 SAT mg/l | Dew Point (degrees C.) | H$_2$0 SAT mg/l | Dew Point (degrees C.) | H$_2$0 SAT mg/l |
|---|---|---|---|---|---|---|---|
| 0.00 | 4.85 | 10.00 | 9.40 | 20.00 | 17.29 | 30.00 | 30.37 |
| 0.56 | 5.04 | 10.56 | 9.73 | 20.56 | 17.86 | 30.56 | 31.29 |
| 1.11 | 5.23 | 11.11 | 10.08 | 21.11 | 18.45 | 31.11 | 32.24 |
| 1.67 | 5.43 | 11.67 | 10.44 | 21.67 | 19.05 | 31.67 | 33.22 |
| 2.22 | 5.64 | 12.22 | 10.81 | 22.22 | 19.67 | 32.22 | 34.22 |
| 2.78 | 5.86 | 12.78 | 11.19 | 22.78 | 20.31 | 32.78 | 35.25 |
| 3.33 | 6.08 | 13.33 | 11.58 | 23.33 | 20.96 | 33.33 | 36.30 |
| 3.89 | 6.31 | 13.89 | 11.98 | 23.89 | 21.64 | 33.89 | 37.37 |
| 4.44 | 6.55 | 14.44 | 12.40 | 24.44 | 22.33 | 34.44 | 38.48 |
| 5.00 | 6.80 | 15.00 | 12.82 | 25.00 | 23.04 | 35.00 | 39.61 |
| 5.56 | 7.05 | 15.56 | 13.27 | 25.56 | 23.77 | 35.56 | 40.78 |
| 6.11 | 7.31 | 16.11 | 13.72 | 26.11 | 24.52 | 36.11 | 41.97 |
| 6.67 | 7.58 | 16.67 | 14.19 | 26.67 | 25.29 | 36.67 | 43.19 |
| 7.22 | 7.86 | 17.22 | 14.67 | 27.22 | 26.09 | 37.22 | 44.44 |
| 7.78 | 8.15 | 17.78 | 15.16 | 27.78 | 26.90 | 37.78 | 45.72 |
| 8.33 | 8.45 | 18.33 | 15.67 | 28.33 | 27.73 | 38.33 | 47.03 |
| 8.89 | 8.75 | 18.89 | 16.20 | 28.89 | 28.59 | 38.89 | 48.38 |
| 9.44 | 9.07 | 19.44 | 16.74 | 29.44 | 29.47 | 39.44 | 49.75 |
| 10.00 | 9.40 | 20.00 | 17.29 | 30.00 | 30.37 | 40.00 | 51.16 |

The control system can use a regression analysis on the data obtained from the learned response to generate the remembered response of the water vapor concentration the enclosure to an air exchange rate of 0.1 laden with water vapor at a concentration of 30 mg/liter. FIG. 20 illustrates this learned response in the form of a graph with best-fit third-order equation.

The simplicity of the dew point control method lies in the fact that it is not necessary to know the actual vapor concentration to be able to bring the water vapor content of the enclosure up to near 99% and control it at this level.

This same methodology will work for combinations of hydrogen peroxide vapor and water vapor. Learned behavior curves (equations) can be generated for various combinations of vapor concentrations and air exchange rates. The control system will use this information to determine how long to remain at a given vaporization concentration and air exchange rate in order to bring the enclosure up to the desired percent saturation. The control will reduce the vaporization concentration and/or the air exchange rate at the predicted time in order to obtain the desired percent saturation without overshooting and exceeding saturation. The dew point sensor feedback will let the control system know that the expected behavior is occurring on a real time basis before the final percent saturation has been achieved.

Maintaining the percent saturation at a maximum will automatically maintain the maximum possible vapor concentration within the enclosure for the given air exchange rate and the given liquid sterilant concentration. Example 2 uses 35% hydrogen peroxide as the liquid sterilant that is being vaporized.

Example 2

Dew Point Control Algorithm

A 50 SCFM air-flow with a vaporization rate of 30 grams/min is used to bring a 1000 cubic foot enclosure up to a near saturation condition. A Dew Point sensor is used to monitor the dew point temperature in the enclosure as sterilant vapors are being introduced. The seasonal maximum enclosure temperature during decontamination is determined to be 28 C. The temperature of pre-heater 80 is adjusted so that the temperature of the carrier air and sterilant vapor exiting the enclosure is 28 C. The introduction of vaporized sterilant is stopped when the dew point temperature reaches about 26 C to avoid exceeding 100% saturation; however, the carrier air-flow continues as the measured sterilant concentration reaches a maximum and begins to fall. FIG. 21 is constructed using the dew point readings to illustrate the dew point behavior that is obtained. A regression analysis produces the dew point curve whose equation is listed on FIG. 21.

The LAG TIME shown on FIG. 21 is the length of time that it takes for the air flowing from the enclosure to reach the maximum dew point temperature (as measured by the dew point sensor) after vaporization was stopped.

The second "learned behavior" run will contain both condition phase and a decontamination phase. The transition from the high condition vaporization rate to the lower decontamination vaporization rate will occur when the dew point temperature reaches 26° C. This transition would take place at a lower temperature if the enclosure temperature were below the maximum of 28° C.

The maximum dew point temperature will occur around "LAG TIME" minutes after the switch to the decontamination vaporization rate if the selected decontamination vaporization rate is not above the optimum vaporization rate (i.e. the vaporization rate that will maintain the dew point temperature at the carrier air temperature). FIG. 22 is for a decontamination vaporization rate of 10 grams/min and FIG. 23 is for a vaporization rate of 12 grams/min.

If the vaporization rate during the decontamination phase exceeds the optimum vaporization rate, the dew point temperature may continue to rise after the LAG TIME has passed into the decontamination phase. FIG. 24 shows how the dew point temperature continues to rise for a decontamination vaporization rate of 13 grams/min.

The control system will look at the dew point temperature and the slope of the dew point graph based upon the last three readings and will reduce the vaporization rate, for example by 5%. The control system will continue to monitor the dew point temperature and the slope of the dew point curve. If, it is still rising, the vaporization rate will be reduced another 5%. If the dew point temperature begins to fall, the vaporization rate will be raised by half of the amount of the last reduction, or 2.5%.

The control system has to be looking forward during the decontamination phase by a length of time equal to two or more LAG TIMES when it is monitoring and controlling the vaporization rate. The amount that the vaporization rate is increased (or decreased) will depend upon the slope of the dew point curve and the difference between the dew point temperature and the air stream temperature. For example, the first injection rate increase might have been around 5% for FIG. 22 but only about 2.5% for FIG. 23.

The LAG TIME will be larger for low air exchange rates and smaller for high air exchange rates. Increasing the air exchange rate (and maintaining the vaporization concentration) will decrease the LAG TIME. The dew point can also be affected by a change in air exchange rate even if the vaporization concentration is maintained.

The shape of the condition and decontamination sections of the dew point graphs will be similar when the temperature of the enclosure is a degree, two or three below the maximum. However, the transition point from the condition phase to the decontamination phase will occur earlier.

FIG. 12 is an embodiment of a liquid sterilant delivery system that has a low cost feedback control. The liquid sterilant is contained in bottle 310. Pump 360 withdraws air from reservoir 320 through conduit 365, valve 364, through pump 360 and valve 368 and out filter 366 creating a vacuum in reservoir 320. Valves 364 and 368 close and isolate the pump from reservoir 320. Valve 314 is opened so that liquid sterilant is drawn from bottle 310, through conduit 312, through valve 314 and into reservoir 320. Pressure transducer PT1 monitors the pressure in reservoir 320. When the pressure reaches the pre-determined level, valve 314 closes and the flow of liquid sterilant into reservoir 320 stops. Valve 376 is open whenever the system is not operating venting any pressure that might build up in reservoir 320 through conduit 374, valve 376 and out filter 378.

When liquid sterilant is being withdrawn from reservoir 320 through dip tube 330 and conduit 388 by pump 390 all other valves are oriented so that no other air or liquid can enter reservoir 320. Pressure transducer PT1 monitors the pressure as liquid is withdrawn from reservoir 320 and the volume of air 350 in reservoir 320 increases. The liquid removal rate is equal to the rate at which air volume 350 increases. The ideal gas law is used to calculate the rate at which air volume 350 increases. After the liquid sterilant passes through pump 390 and conduit 395 it enters ultra-sonic nozzle 80. Ultrasonic nozzle 80 transforms the liquid sterilant into a fine mist and discharges it into the hot recirculating air stream. (Refer to FIG. 8, 9, 17 or 19).

The volume of air 350 in sterilant reservoir 320 needs to be known before liquid can be added to or removed from the reservoir. This volume is calculated based upon the readings of pressure transducers PT1 and PT2 and the known volume of air in reservoir 355 using equation 5. (Equation 5 is the same as equation 1(a).)

$$V_{350} = \frac{PT1_i - PT1_f}{PT2_f - PT2_i} * V_{355} \quad \text{Equation 5}$$

Where
$PT1_i$ is the initial pressure of the air in reservoir 320
$PT1_f$ is the final pressure of the air in reservoir 320
$PT2_f$ is the final pressure of the air in reservoir 355
$PT2_i$ is the initial pressure of the air in reservoir 355
$V_{355}$ is the known volume of reservoir 355
$V_{350}$ is the unknown volume of air in reservoir 320

Reservoir 320 is initially pressurized to pressure $PT1_i$ by pump 360 that draws air in through filter 362, valve 364, through pump 360 out valve 368 and into reservoir 320 until the desired pressure is reached as measured by pressure transducer PT1. All valves to reservoir 320 are then closed, isolating reservoir 320. Valve 380 is opened, venting reservoir 355 to atmospheric pressure $PT2_i$ through filter 382. Pressures $PT1_i$ and $PT2_i$ are recorded. Valve 380 is switched connecting reservoir 355 to the air 350 in reservoir 320. The pressure in the two reservoirs equilibrates isothermally to $PT1_f$ and $PT2_f$. Since $PT1_f$ and $PT2_f$ should be equal, a comparison of the pressure sensor readings is made to ensure that both pressure transducers are working properly. Equation 5 is then used to calculate the volume of air 350 in reservoir 320. The volume of liquid sterilant in reservoir 320 is equal to the volume of the reservoir less the calculated volume of air in sterilant reservoir 320.

Changes in the volume of fluid in reservoir 320 are made indirectly by monitoring the pressure in reservoir 320 and using the changes in the pressure to calculate the changes in air volume 350. The change in liquid sterilant volume is equal to the change in air volume.

$$V_{350} \text{ at time } T = \frac{PT1_{initial}}{PT1 \text{ at time } T} * V_{350\,initial} \quad \text{Equation 6}$$

Equation 6 is used when liquid sterilant is being added to reservoir 320 and when liquid sterilant is being withdrawn from reservoir 320. A rotary encoder (not shown) can be used to monitor the rotational speed of the pump and maintain it at a speed that is adjusted periodically based upon equation 6 because the accuracy of peristaltic tubing varies with fluid temperature, inlet pressure, cumulative number of pump rotations on the tubing segment, output pressure and rotational speed. Valve 325 is opened whenever reservoir 320 needs to be drained.

FIG. 13 is an alternative embodiment of the liquid sterilant delivery system and feedback control. Air reservoir 355 has been re-located to be in intimate contact with the liquid sterilant in reservoir 320 to ensure that the temperature of air volume 350 is the same as the temperature of air volume 355. Three-way valve 380 has been replaced by two 2-way valves 380a and 380b that serve the same functional purpose of three-way valve 380.

Air pump 30 from FIGS. 8 and 9 needs to produce an airflow that can be varied by control system 1000 when needed. The backpressure, or flow resistance, in the conduits leading into and out of the enclosure can make it very difficult to identify and select an air pump that meets the requirements that will allow it to be connected to virtually any enclosure. FIG. 14 is an exploded view of a water ring pump that can produce a wide range of flows against backpressures that would stall most centrifugal blowers. Motor 600 turns shaft 610 and rotor 630. The rotational motion of rotor 630 throws a flowing ring of water out against housing 640 sealing the tips of the blades on rotor 630. FIG. 15 shows that the air that is contained in volume V1 is compressed by the counter-clockwise rotation of eccentrically placed rotor 630 in housing 640. As rotor 630 continues to rotate counter-clockwise volume V1 makes it to location V2 where outlet port 650 is uncovered. The compressed air contained in volume V2 exhausts through outlet port 650 until the pressure within the pump equals the backpressure in the exhaust conduit. As rotor 620 continues to rotate counter-clockwise the volume between the water seal and rotor 620 expands creating a suction that draws air into the pump housing when inlet port 660 is uncovered. Increasing the rotational speed of motor 600 increases the output flow rate of the pump. Increasing the ratio of the inlet volume to the outlet volume, V1/V2, will increase the output flow of the pump as well as the backpressure against which the pump can operate. The pump does not have any seals that can be damaged by the vaporized and condensed sterilant so it will have a long life expectancy. The motor can be directly coupled to shaft 610 or it can be magnetically coupled to prevent liquid from ingressing into the motor windings.

FIG. 19 is a schematic of an alternate embodiment of the invention that pulls the air stream from enclosure 1 through filter 2, outlet-port 3, and conduit 4 into inlet 10 of the humidity and decontaminant vapor control system 900. Isolation valve 6 is open during a decontamination cycle so that the flow of gas is drawn into sparger(s) 30 in cold-water bath 800 whose operation was previously described in conjunction with FIGS. 18(*a*) and 18(*b*). Air blower 20 creates a negative pressure on the top of cold-water bath 800 drawing the air bubbles up through the water bath. Air blower 20 is shown downstream of heat exchanger 60 (condenser 160) but could be located upstream of heat exchanger 60 (Condenser 160). Heat exchanger 60 (Condenser 160) heats the air stream as it passes through. Blower 20 also heats the air stream so that it's temperature is in excess of 100° F. when it passes through conduit 901 and enters conduit 70, which contains process air heater 75, and temperature sensor T1. If necessary, heater 75 finishes elevating the temperature of the carrier air stream to the desired temperature as measured by temperature sensor T1. The desired temperature will be equal to the enclosure ambient temperature except when atomized sterilant is being introduced into the air stream. The temperature of the carrier air stream will be elevated whenever atomized sterilant needs to be vaporized. Atomizer 80, which is preferably an ultrasonic nozzle, delivers atomized liquid sterilant into the heated carrier air stream when a decontamination cycle is in the condition or sterilize phases. Temperature sensor T2 monitors the temperature of the vaporization process within the carrier air stream and can be used to provide closed loop feedback to control the temperature of air process heater 75. Carrier air flow sensor 90 monitors the airflow rate in conduit 100 just before it passes through isolation valve 8, as the sterilant laden air stream is returned to enclosure 1 through conduit 7 and filter 9. The sterilant-laden air passes through enclosure 1, through filter 2 and outlet port 3, down conduit 4 and back into humidity and decontaminant vapor control system 900.

Optional bypass conduit 11 can be used to connect inlet 10 to outlet 100 if isolation valves 6 and 8 are three way valves with the third port being connected to the ends of conduit 11. Sealed enclosure 1 is isolated from humidity and decontaminant system 901 in the bypass mode.

The embodiment of the present invention shown in FIG. 19 is more energy efficient than the embodiments shown in FIG. 8. 9 or 17 because the thermal energy from the blower will be imparted into the air stream on the downstream side of the cold water bath where it needs to be heated prior to the introduction of the sterilant. The air blower also will not be exposed to the vapor decontaminant, and any air that may escape past the shaft seals in the motor would not contain any decontaminant vapor.

The invention claimed is:

1. A method of decontaminating the interior of a sealable enclosure and the contents thereof comprising:
   a. providing a sealable enclosure and processing means associated therewith;
   b. sealing said enclosure from fluid communication with unfiltered gas;
   c. drawing gas into said processing means through an inlet port,
   d. establishing a flow of filtered gas from said processing means, through a first conduit to said sealed enclosure, through said sealed enclosure, and out an outlet port in said sealed enclosure to a decontaminant vapor disposing means;
   e. conditioning said flow of filtered gas by pushing, or pulling, it through a constant temperature water based bath contained within said processing means utilizing an air moving means that is also contained within said processing means;
   f. continuing the conditioning of said flow of filtered gas until the humidity of all of the gas within said sealed enclosure approaches that of the gas exiting the water-based bath;
   g. introducing a multi-component vapor decontaminant, one component of which is water, into said flow of filtered gas at a first introduction rate so that said flow of gas carries said vapor decontaminant through said first conduit into, through and out of said enclosure;
   h. continuing the introduction of decontaminant vapor until the percent saturation of said flowing gas stream within said enclosure starts to approach, or is predicted to approach, 100 percent;
   i. controlling the rate at which said decontaminant vapor is introduced into said flowing gas stream using a feed forward control system to maintain the percent saturation just below 100 percent;
   j. maintaining the flow of gas and decontaminant vapor into and through said sealable enclosure at least long enough to decontaminate the sealable enclosure and its contents.

2. The method of claim 1 wherein the flow of gas from the outlet port of the sealable enclosure is directed back to the inlet port of said processing means.

3. The method of claim 1 wherein the sealable enclosure is pressurized/evacuated slightly to control the flow of air from/into the enclosure through any openings.

4. The method of claim 3 wherein the sealable enclosure is constructed such that it allows objects to enter through openings in the enclosure, pass through the enclosure and exit through openings in the enclosure.

5. The method of claim 4 wherein the length of time that it takes objects to pass through the enclosure is sufficient to decontaminate the objects.

6. The method of claim 5 wherein the flow of decontaminant laden gas can be directed into cavities, or through passages, in the objects passing through said enclosure so that all of the surfaces that come in contact with the gas can be decontaminated.

7. The method of claim 6 wherein said enclosure is a production line in a medical device, pharmaceutical, food, or beverage manufacturing plant.

8. The method of claim 1 wherein the sealed enclosure is an entity or part of an entity, such as a surgical suite in a hospital, a patient room in a hospital or nursing home, an ambulance, a military tank, an air handling system in a building, areas in a cruise ship, etc that need to be decontaminated before being used again.

9. The method of claim 1 wherein further comprising a peristaltic pump delivers liquid sterilant to an ultra sonic nozzle that introduces a fine mist of sterilant liquid into the flowing air stream where it then vaporizes.

10. The method of claim 1 wherein further comprising reservoir and reference chamber pressure measurements and calculations are used as feedback to monitor and control the rate at which the liquid decontaminant is vaporized.

11. The method of claim 1, wherein the multi-component sterilant is comprised of hydrogen peroxide and water.

12. The method of claim 1 wherein the temperature of the flowing air stream is elevated before the vapor decontaminant of the sterilant liquid is introduced.

13. The method of claim 1 wherein the temperature of the flowing air stream is controllably elevated in order to maintain the temperature of the generated vapor contaminant air stream at a particular value.

14. The method of claim 1 wherein the feed forward control system is comprised of a "learned" and "remembered" behavior.

15. The method of claim 1 wherein conditioning comprises
   a. Humidifying the said flow of air if its initial humidity level is below that which would be produced by flowing it through the constant temperature water bath;
   b. Dehumidifying the said flow of air if its initial humidity level is above that which would be produced by flowing it through the constant temperature water bath;
   c. Leaving the humidity level of said flow of air unchanged if its initial humidity level is equal to that which would be produced by flowing it through the constant temperature water bath.

16. A method of decontaminating the interior of a sealable enclosure and the contents thereof comprising:
   a. providing a sealable enclosure and processing means associated therewith;
   b. sealing said enclosure from fluid communication with unfiltered gas;
   c. drawing gas into said processing means through an inlet port,
   d. establishing a continuous flow of filtered gas from said processing means, through a first conduit to said sealed enclosure, through said sealed enclosure, and out an outlet port in said sealed enclosure;
   e. controlling the humidity of said continuous flow of filtered gas by pushing, or pulling, it through the humidity control apparatus until the humidity of all of the gas within said sealed enclosure approaches that of the gas exiting the humidity control apparatus;
   f. introducing a multi-component vapor decontaminant, one component of which is water, into said flow of gas at a first introduction rate so that said flow of gas carries said vapor decontaminant through said first conduit into, through and out of said enclosure;
   g. continuing the introduction of decontaminant vapor until the percent saturation of said flowing gas stream within said enclosure starts to approach 100 percent as measured by a chilled mirror hygrometer;
   h. controlling the rate at which said decontaminant vapor is introduced into said flowing gas stream using a feed forward control system to maintain the percent saturation just below 100 percent as measured by a chilled mirror hygrometer;
   i. maintaining the continuous flow of gas and decontaminant vapor into and through said sealable enclosure to decontaminate the sealable enclosure and its contents.

17. The system of claim 16 wherein the humidity control apparatus is a sparger submerged in a water-based bath that is chilled by a refrigeration system.

18. The system of claim 17 wherein the water-based bath has a freezing point that is lower than 32° F. (0° C.).

19. The system of claim 18 wherein the multi-component sterilant is comprised of hydrogen peroxide and water.

20. A flowing gas vapor generation system comprising:
   a. at least one inlet port for air to be drawn into said system;
   b. at least one outlet port for air to be discharged from said system;
   c. at least one means for drawing a stream of air into said system and discharging said stream of air from said system;
   d. a means of measuring and controlling the air stream flow rate;
   e. at least one water bath through which all, or part, of the stream of air flows when it passes through said system;
   f. a means for monitoring and maintaining the temperature of the water bath;
   g. a means for breaking the stream of air that passes through the water bath into small bubbles;
   h. a means for monitoring and controlling the temperature of the flowing air stream;
   i. a means for vaporizing a multi-component sterilant, one component of which is water, and introducing it into said flowing air stream;
   j. a means for measuring and controlling the vaporization rate of said multi-component sterilant;
   k. a means for measuring the percent saturation of the stream of air and adjusting the sterilant injection rate, the air flow rate, or the air temperature based upon the percent saturation;
   l. a control system that is capable of receiving signals from said monitor means and directing said control means using a feed forward control scheme.

* * * * *